United States Patent
Martchenko et al.

(10) Patent No.: US 10,369,119 B2
(45) Date of Patent: Aug. 6, 2019

(54) INHIBITION OF MULTIPLE PATHOGENIC AGENTS USING BITHIONOL

(71) Applicant: KECK GRADUATE INSTITUTE OF APPLIED LIFE SCIENCES, Claremont, CA (US)

(72) Inventors: Mikhail Martchenko, Claremont, CA (US); William Leonardi, Rosemead, CA (US)

(73) Assignee: Keck Graduate Institute of Applied Life Sciences, Claremont, CA (US)

( * ) Notice: Subject to any disclaimer, the term of this patent is extended or adjusted under 35 U.S.C. 154(b) by 0 days.

(21) Appl. No.: 15/770,142

(22) PCT Filed: Oct. 21, 2016

(86) PCT No.: PCT/US2016/058216
§ 371 (c)(1),
(2) Date: Apr. 20, 2018

(87) PCT Pub. No.: WO2017/070538
PCT Pub. Date: Apr. 27, 2017

(65) Prior Publication Data
US 2018/0303769 A1 Oct. 25, 2018

Related U.S. Application Data

(60) Provisional application No. 62/321,089, filed on Apr. 11, 2016, provisional application No. 62/244,601, filed on Oct. 21, 2015.

(51) Int. Cl.
| | |
|---|---|
| *A61K 31/10* | (2006.01) |
| *A61P 31/14* | (2006.01) |
| *A61P 31/04* | (2006.01) |
| *A61K 38/14* | (2006.01) |
| *A61K 45/06* | (2006.01) |
| *A61K 31/4164* | (2006.01) |
| *A61K 31/43* | (2006.01) |
| *A61K 31/496* | (2006.01) |
| *A61K 31/546* | (2006.01) |
| *A61K 31/65* | (2006.01) |
| *A61K 31/7048* | (2006.01) |
| *A61K 31/7056* | (2006.01) |
| *A61K 31/131* | (2006.01) |

(52) U.S. Cl.
CPC .......... *A61K 31/10* (2013.01); *A61K 31/4164* (2013.01); *A61K 31/43* (2013.01); *A61K 31/496* (2013.01); *A61K 31/546* (2013.01); *A61K 31/65* (2013.01); *A61K 31/7048* (2013.01); *A61K 31/7056* (2013.01); *A61K 38/14* (2013.01); *A61K 45/06* (2013.01); *A61P 31/04* (2018.01); *A61P 31/14* (2018.01); *A61K 31/131* (2013.01); *A61K 2300/00* (2013.01); *Y02A 50/391* (2018.01); *Y02A 50/469* (2018.01)

(58) Field of Classification Search
CPC .................................................... A61K 31/10
See application file for complete search history.

(56) References Cited

U.S. PATENT DOCUMENTS

2015/0164873 A1* 6/2015 Qu ....................... A61K 31/095
514/259.2

OTHER PUBLICATIONS

Cruz, Treatment of Human Taenisasis in the Phillipines: A Review. The Southeast Asian Journal of Tropical Medicine and Public Health, Dec. 1991; vol. 22 Supp., p. 271-244.*
Ayyagari et al, Bithionol Inhibits Ovarian Cancer Cell Growth in Vitro—Studies on Mechanism(s) of Action, BMC Cancer, Feb. 4, 2014; 14(61): 1-17.*
Ayyagari, V.N. et al., Bithionol Inhibits Ovarian Cancer Cell Growth in Vitro—Studies on mechanism(s) of Action. BMC Cancer, Feb. 4, 2014; vol. 14, No. 61; pp. 1-17.
Cordoba-Rodriguez, R. et al., Anthrax Lethal Toxin Rapidly Activates Caspase-1/ICE and Induces Extracellular Release of Interleukin (IL)-Ibeta and IL-18, The Journal of Biological Chemistry, Mar. 9, 2004; vol. 279, No. 20; pp. 20563-20566.
Cruz, A.C, Treatment of Human Taeniasis in the Phillipines: A Review. The Southeast Asian Journal of Tropical Medicine and Public Health, Dec. 1991; vol. 22 supplemental; pp. 271-274.
(Leonardi, W. et al.) Bithionol Blocks Pathogenicity of Bacterial Toxins, Ricin, and Zika Virus, Scientific Reports, Sep. 30, 2016; vol. 6, No. 34475; pp. 1-12.
Wahome, P.G. et al., Identification of Small Molecules That Suppress Ricin-Induced Stress-Activated Signaling Pathways, PLoS One, Nov. 1, 2012; vol. 7, No. 11; pp. 1-8.
International PCT Search Report and Written Opinion issued in corresponding International PCT Application No. PCT/US2016/058216, dated Jan. 17, 2017, 8 pages.

* cited by examiner

*Primary Examiner* — Svetlana M Ivanova
(74) *Attorney, Agent, or Firm* — Umberg Zipser LLP

(57) ABSTRACT

Compositions and methods including Bithionol are provided for treating, inhibiting, or preventing caspase-dependent pathogenic agents in a host cell or infected subject. Examples of caspase-dependent pathogenic agents include ricin, anthrax toxin, Botulinum neurotoxin A, diphtheria toxin, *Pseudomonas aeruginosa* exotoxin A, cholera toxin, Zika virus, and combinations thereof. Compositions and methods also include Bithionol in combination with an antibiotic for more effective clearance of the pathogen and/or toxins.

19 Claims, 24 Drawing Sheets
(15 of 24 Drawing Sheet(s) Filed in Color)

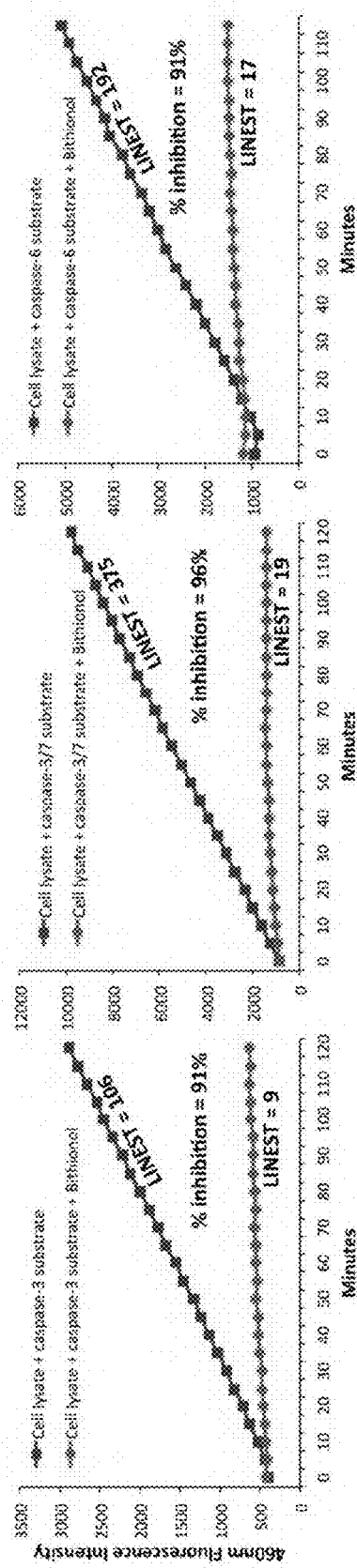

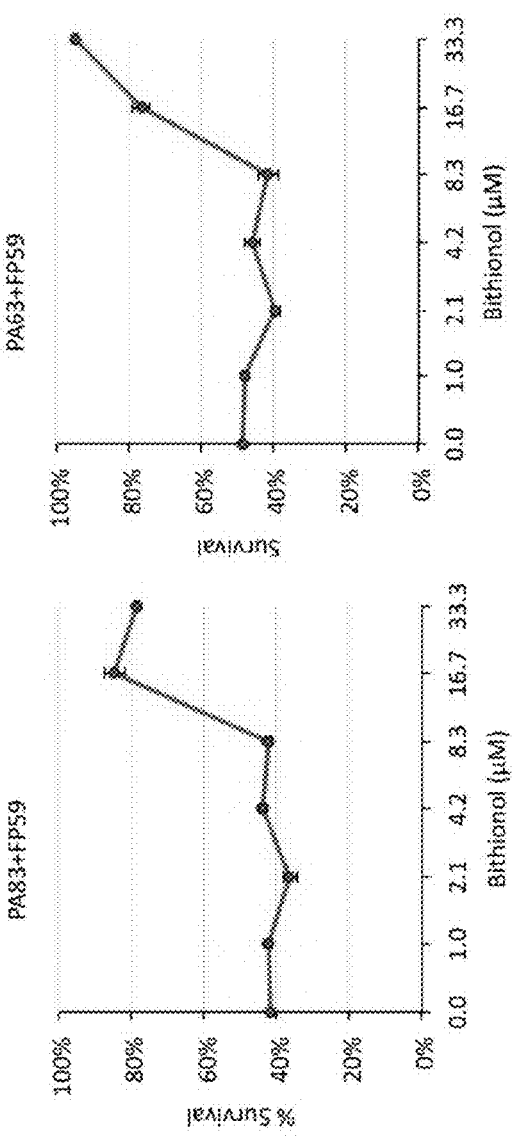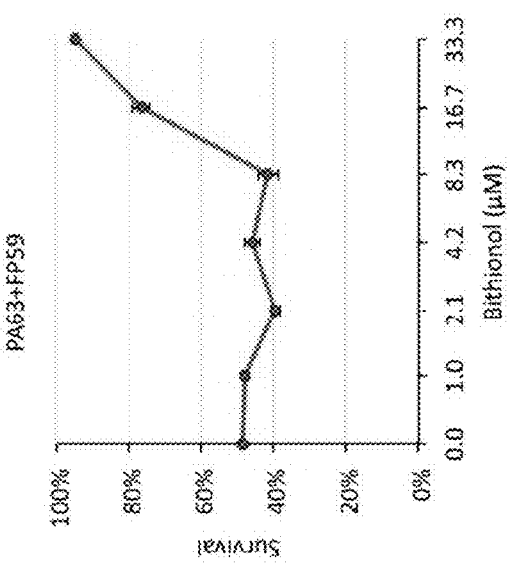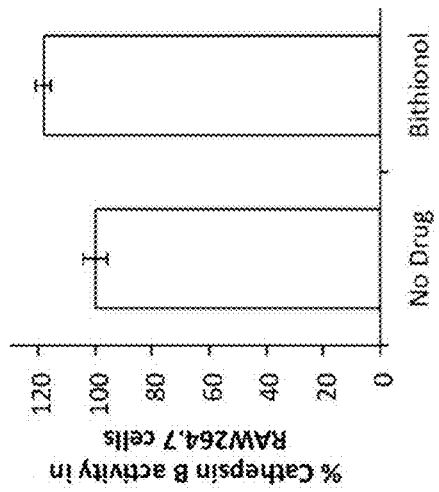

FIG. 6E

| Drug | Cells | Virus (strain) | EC50, μM | SD, μM |
|---|---|---|---|---|
| Bithionol | Vero E6 | Zika (Puerto Rico) | 6.66 | 1.15 |
| Bithionol | Vero E6 | Zika (Senegal) | 5.52 | 0.29 |
| Bithionol | Human Astrocytes | Zika (Senegal) | 6.28 | 0.22 |

INHIBITION OF MULTIPLE PATHOGENIC AGENTS USING BITHIONOL

CROSS-REFERENCE TO RELATED APPLICATION(S)

This application is a U.S. National Phase Patent Application and claims priority to and the benefit of International Application Number PCT/US2016/058216, filed on Oct. 21, 2016, which claims priority to and the benefit of U.S. Provisional Application Ser. No. 62/244,601 filed on Oct. 21, 2015, entitled "Identification of Broad-Spectrum Therapies Targeting Overlaps of Pathogens and Host Proteins," and U.S. Provisional Application Ser. No. 62/321,089 filed on Apr. 11, 2016, entitled "Inhibition of Multiple Pathogens Using Bithionol," the entire contents of all of which are incorporated herein by reference.

BACKGROUND

In recent years, a better understanding of protein interaction networks has led to the identification of highly connected hub proteins and pathways that are commonly used by a number of different pathogens and in a range of diseases. These hubs represent promising targets for drug development as depicted in FIG. 1A.

Most disease networks have the "small-world" property, where proteins are only a few interactions away from any other proteins. Therefore, inhibiting a given node can potentially affect the state of most nodes in its vicinity as well as the activity of the network itself. In this way, therapeutic inhibition of nodes and hubs within one disease network can affect other disease modules or pathways.

Cytotoxic bacterial and plant toxins have evolved to exploit host proteins and cellular pathways that mediate the entry of those toxins into host cells and to induce cell-death. Although toxins exploit unique host pathways, these pathways are interconnected. For example, while anthrax, diphtheria, and Botulinum toxins reach the cytoplasm from acidified endosomes, cholera, *Pseudomonas aeruginosa* and ricin toxins are transported into the cytoplasm through the host ER-associated degradation pathway. These pathways interconnect at host "hub" proteins. It is known that multiple infectious pathogens or toxins that negatively affect hosts by different mechanisms exploit the same host pathways. Accordingly, it is feasible for multiplex approaches to lead to the discovery of a therapy for broadly active and host-oriented infectious diseases that target the host function being exploited by multiple pathogenic agents.

SUMMARY

In some embodiments of the present invention, a method of inhibiting a pathogenic agent in a host cell or in a subject includes administering Bithionol to the host cell or the subject, the pathogenic agent being selected from ricin, anthrax toxin, Botulinum neurotoxin A, diphtheria toxin, *Pseudomonas aeruginosa* exotoxin A, cholera toxin, Zika virus, or combinations thereof.

In some embodiments of the present invention, a method of inhibiting a pathogenic agent in a host cell or in a subject includes administering Bithionol to the host cell or the subject, the pathogenic agent being selected from ricin, anthrax toxin, or Zika virus.

In some embodiments of the present invention, a method of inhibiting a caspase-dependent pathogenic agent in a host cell or in a subject includes administering Bithionol to the host cell or the subject.

In some embodiments of the present invention, a composition for inhibiting a caspase-dependent pathogenic agent in a host cell or a subject includes Bithionol and an antibiotic.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 4A is a graph showing the amount of fluorescence intensity from two FRET cell lysate reactions in which caspase-3 containing cellular lysate cleaves fluorescently labeled substrate peptide without drugs (blue squares), or in the presence of 33 µM Bithionol (red squares), according to embodiments of the present invention.

FIG. 4B is a graph showing the amount of fluorescence intensity from two FRET cell lysate reactions in which caspase-3/7 containing cellular lysate cleaves fluorescently labeled substrate peptide without drugs (blue squares), or in the presence of 33 µM Bithionol (red squares), according to embodiments of the present invention.

FIG. 4C is a graph showing the amount of fluorescence intensity from two FRET cell lysate reactions in which caspase-6 containing cellular lysate cleaves fluorescently labeled substrate peptide without drugs (blue squares), or in the presence of 33 µM Bithionol (red squares), according to embodiments of the present invention.

FIG. 5D is a graph showing the percent survival of RAW264.7 cells using an MTT assay, in which the RAW264.7 cells were pretreated with the indicated dose of Bithionol for 1 hour, followed by a 6 hours intoxication with 0.5 µg/ml 83 kDa PA+FP59, with cell viability determined by MTT assay and shown as the percentage of survivors relative to cells not treated with Bithionol, according to embodiments of the present invention.

FIG. 5E is a graph showing the percent survival of RAW264.7 cells using an MTT assay, in which the RAW264.7 cells were pretreated with the indicated dose of Bithionol for 1 hour, followed by a 6 hours intoxication with 0.5 µg/ml Furin processed 63 kDa PA+FP59, with cell viability determined by MTT assay and shown as the percentage of survivors relative to cells not treated with Bithionol, according to embodiments of the present invention.

FIG. 5F is a graph showing the amount (percent) of cathepsin-B activity in RAW264.7 cells using a FRET assay, in which the RAW264.7 cells were treated with 33 µM Bithionol of DMSO for 1 hour prior to lysis, and determination of cathepsin B activity was assessed by FRET assay, according to embodiments of the present invention.

FIG. 6E is a table summarizing the EC50 concentrations of Bithionol on the pathogenicity of Zika Virus in Vero E6 and human astrocytes, according to embodiments of the present invention.

DETAILED DESCRIPTION

Using a cell-based multiplex approach to screen a library of FDA-approved drugs for inhibition of disparately acting pathogens, Bithionol, which was previously used clinically to treat helminths (parasitic worms), is shown to inhibit the pathogenic agents by inhibiting host caspases. A depiction of the disclosed study of known host pathways and host proteins exploited by pathogens (HPEP) is shown in FIGS. 1B and 2A-2D forming the basis for results shown in this disclosure and embodiments of the present invention.

According to embodiments of the present invention, Bithionol reduces or prevents the pathogenicity of a wide range of pathogenic agents, including ricin, anthrax lethal toxin, Botulinum neurotoxin A, diphtheria toxin, *Pseudomonas aeruginosa* exotoxin A, cholera toxin, and Zika virus.

As used herein, the term "pathogen" or "pathogenic agent" refers to a virus or bacteria, and may also include the "toxins of the pathogen." For example, inhibition of an endocytic pathogen includes inhibition of the pathogen and inhibition of the toxins of the pathogen.

As used herein, *Bacillus anthracis* refers to the bacterium and anthrax toxin or toxins refer to the pathogenic agents. Anthrax toxins include the protective antigen (PA) and lethal factor (LF). As used herein, *Clostridium botulinum* or *C. botulinum* refers to the bacterium and botulinum refers to the toxin. As used herein *Vibrio cholerae* refers to the bacterium and cholera refers to the toxin. As used herein, *Corynebacterium diphtheriae* or *C. diphtheriae* refers to the bacterium and diphtheria refers to the toxin. As used herein, *Pseudomonas aeruginosa* or *P. aeruginosa* refers to the bacterium and *Pseudomonas aeruginosa* exotoxin A or (PE) refers to the toxin.

Figure 6A:
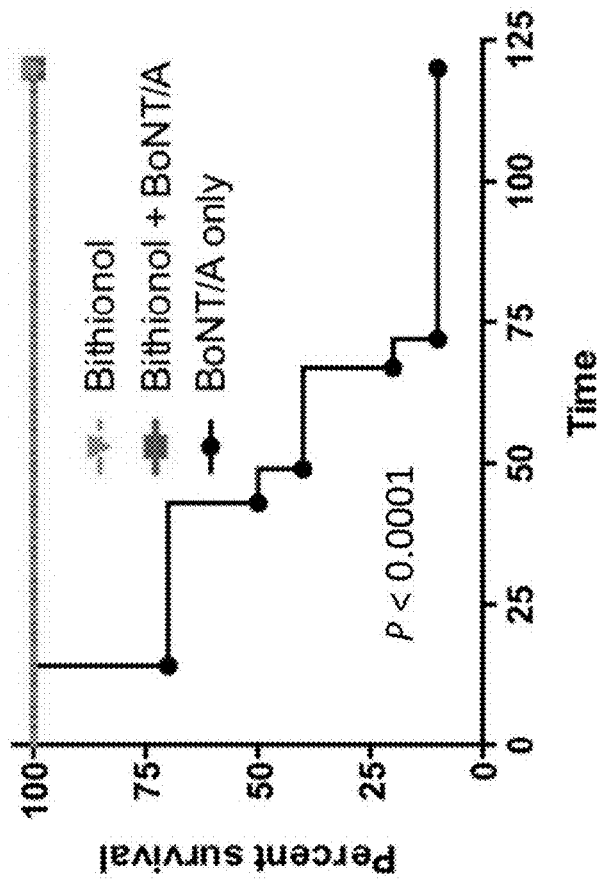
FIG. 6A is a graph of the amount (percent) of cell survival measured by FSC/SSC flow cytometry in human K562 cells incubated with the indicated doses of Bithionol for 2 hours, and then challenged with ricin for 24 hours, according to embodiments of the present invention.
Figure 6B:
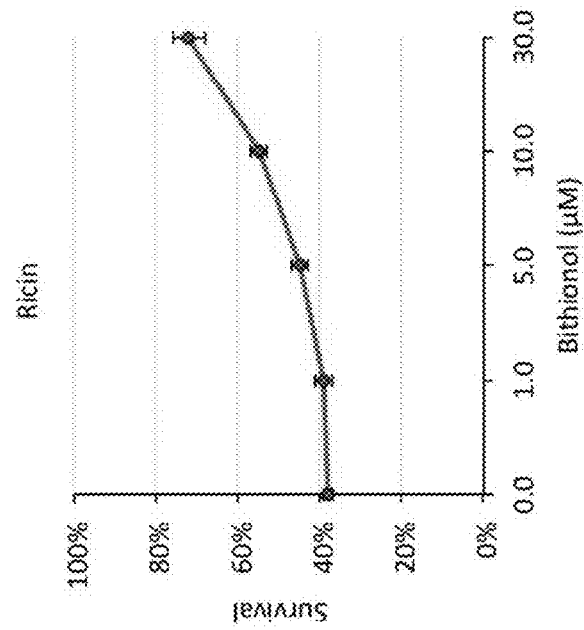
FIG. 6B is a graph showing percent survival of 10 Swiss Webster CFW mice treated with 6 mg/kg Bithionol in the presence (BoNT/A only: black) or absence of botulinum neurotoxin serotype A complex (BoNT/A) by oral gavage (Bithionol only: green; Bithionol and BoNT/A: red) over a period of 7 days, with the Bithionol and BoNT/A survival curves are statistically different based on the Log-rank (Mantel-Cox) test, P<0.0001, according to embodiments of the present invention.

The term "prevent," and like terms, as used herein, refers to all activities that inhibit pathogenicity or retard or reduce pathogenesis of a pathogen infection by administering a composition according to embodiments of the present invention, which includes at least Bithionol and optionally another composition as disclosed herein. That is, the term "prevent" refers to a lack of pathogenesis, or to inhibition of pathogenesis, including inhibition of pathogenic agents or toxins. For example, as shown in FIG. 6B, all of the mice that received Bithionol (at 6.0 mg/kg) and botulinum neurotoxin serotype A (BoNT/A complex) (3 ug/mouse) survived, therefore evidencing that the administration of Bithionol prevented death of these mice when exposed to botulinum toxin. In contrast, mice only receiving BoNT/A complex (3 ug/mouse) without Bithionol, died.

As used herein, "treat," "treating," "treatment," and like terms refer to a method of reducing the effects of pathogenesis resulting from infection by a pathogen (e.g., a caspase-dependent pathogen), and refers to all activities to improve, alleviate or otherwise favorably change the symptoms resulting from an infection by a pathogen by administration of a composition that includes at least Bithionol, and optionally another composition, as described herein.

As used herein, "subject" includes, but is not limited to, animals, including humans. The subject may be a vertebrate, for example, a mammal. The term "subject" does not denote a particular age or sex. Thus, adult and newborn subjects, as well as fetuses, whether male or female, are included in the term "subject."

In some embodiments of the present invention, Bithionol is administered to a cell or a subject infected with a caspase-dependent pathogen, thereby inhibiting the pathogen-related cell death and disease. For example, caspase inhibition in the presence of Bithionol is shown for caspase-3, caspase-6, caspase-7, and caspase-1 in FIGS. 4A-4C and 5B, respectively. Non-limiting examples of caspase-dependent pathogenic agents (pathogens or toxins) include ricin, anthrax lethal toxin, Botulinum neurotoxin A, diphtheria toxin, *Pseudomonas aeruginosa* exotoxin A, cholera toxin, Zika virus, or combinations thereof. In some embodiments, the caspase-dependent pathogenic agents include ricin, anthrax lethal toxin, Zika virus, or combinations thereof.

Figure 4D:
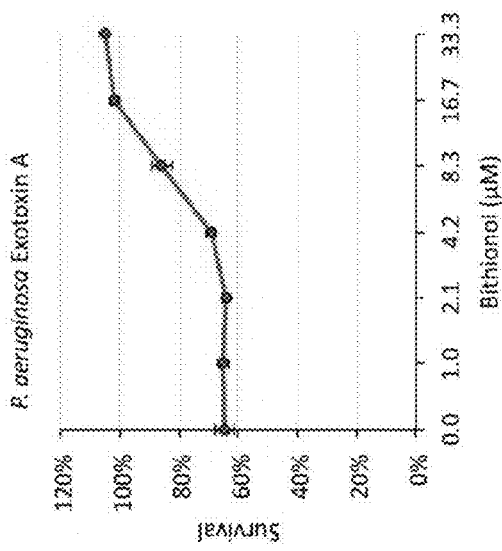
FIG. 4D is a graph showing the percent survival of C32 cells using an MTT assay, in which the C32 cells were pretreated with the indicated dose of Bithionol for 1 hour, followed by Diphtheria toxin for 24 hours, with cell viability determined by MTT assay and shown as the percentage of survivors relative to cells not treated with Bithionol, according to embodiments of the present invention.
Figure 4E:
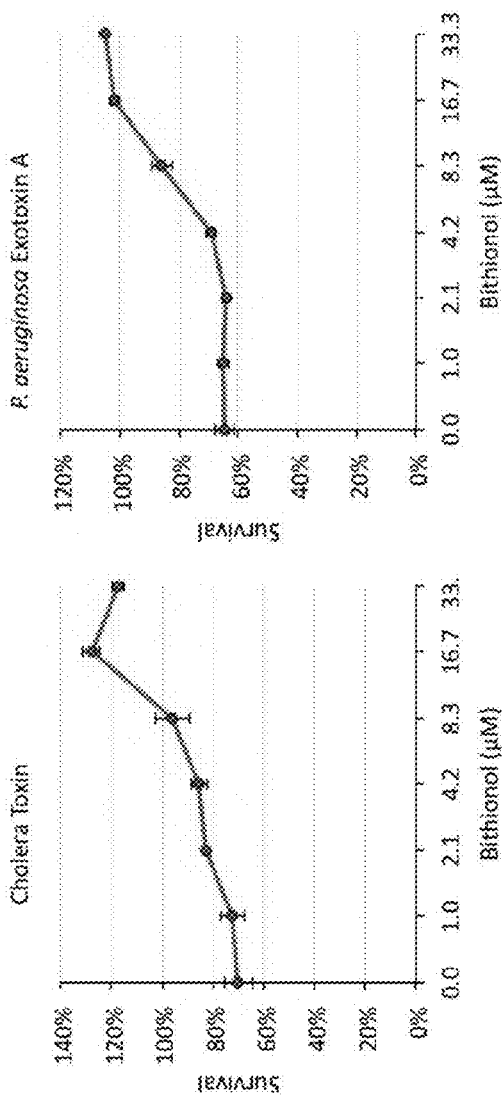
FIG. 4E is a graph showing the percent survival of RAW264.7 cells using an MTT assay, in which the RAW264.7 cells were pretreated with the indicated dose of Bithionol for 1 hour, followed by 12 hours intoxication with cholera toxins, with cell viability determined by MTT assay and shown as the percentage of survivors relative to cells not treated with Bithionol, according to embodiments of the present invention.
Figure 4F:
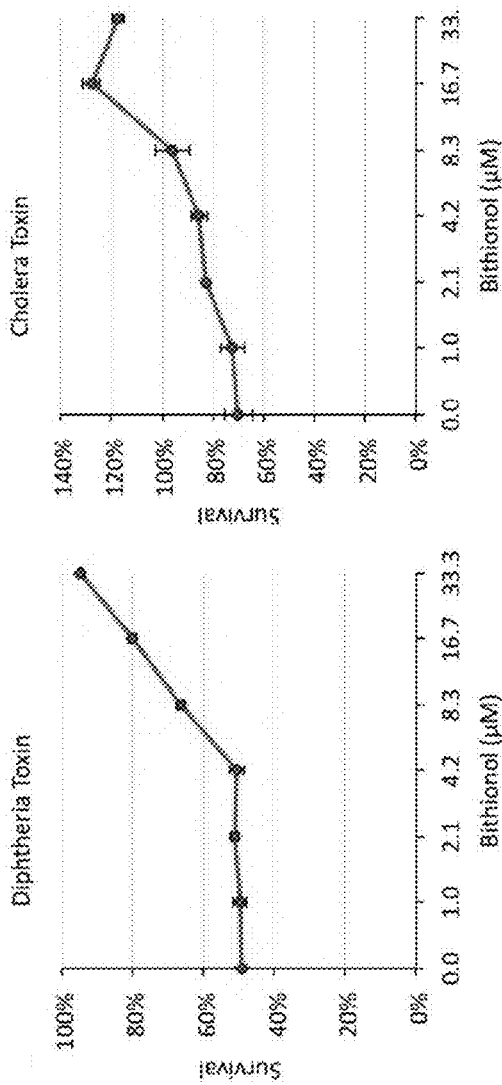
FIG. 4F is a graph showing the percent survival of RAW264.7 cells using an MTT assay, in which the RAW264.7 cells were pretreated with the indicated dose of Bithionol for 1 hour, followed by 12 hours intoxication with Pseudomonas toxin, with cell viability determined by MTT assay and shown as the percentage of survivors relative to cells not treated with Bithionol, according to embodiments of the present invention.
Figure 5B:
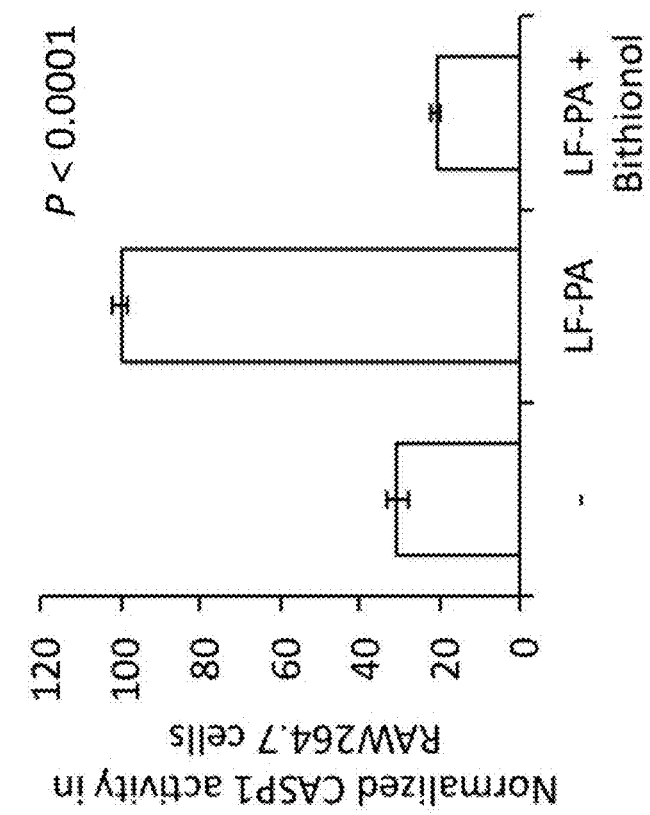
FIG. 5B is a graph showing the normalized caspase-1 activity in RAW264.7 cells using a FRET assay, in which the RAW264.7 cells were treated with LF-PA for 1 hour, and then treated either with 33 µM Bithionol or DMSO for 1 hour prior to lysis and determination of caspase-1 activity, according to embodiments of the present invention.
Figure 5A:
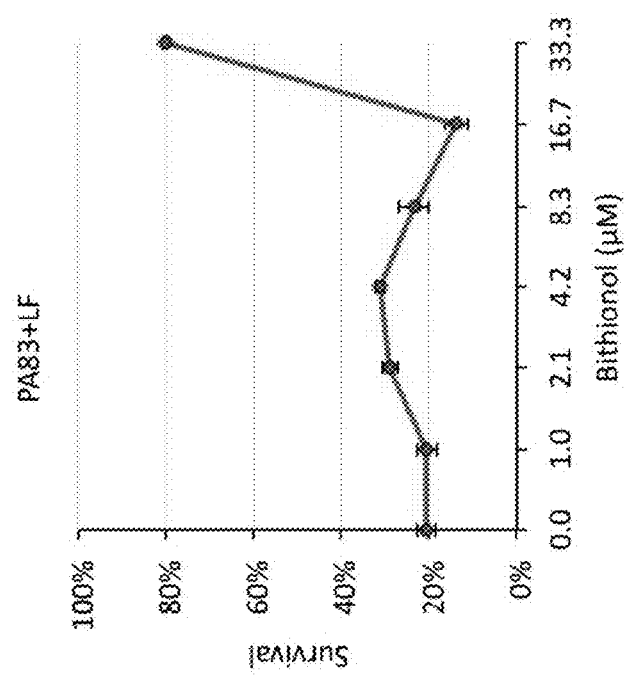
FIG. 5A is a graph showing the percent survival of RAW264.7 cells using an MTT assay, in which the RAW264.7 cells were pretreated with the indicated dose of Bithionol for 1 hour, followed by 6 hours intoxication with anthrax toxin PA-LF, with cell viability determined by MTT assay and shown as the percentage of survivors relative to cells not treated with Bithionol, according to embodiments of the present invention.

Bithionol inhibition of Diphtheria toxin is evidenced by the increased survival of human C32 cells in FIG. 4D. Bithionol is also shown to increase survival of RAW264.7 macrophage cells infected with cholera (FIG. 4E) or *Pseudomonas* (FIG. 4F) toxins. Bithionol inhibition of the cytotoxicity of anthrax toxin and ricin toxin is shown in FIGS. 5A and 6A, respectively. As an example of in vivo analysis, Bithionol was shown to increase the survival of Swiss Webster CFW mice infected with botulinum neurotoxin serotype A complex (BoNT/A) FIG. 6B).

Bithionol was previously used for the treatment of helminths at approximately 30-50 mg/kg/day. Accordingly, in some embodiments of the present invention, a method of inhibiting or preventing a caspase-dependent pathogen in a host cell or in a subject, includes administering about 4.2 uM to about 33.3 uM, or about 1.5 mg/kg/day to about 50.0 mg/kg/day of Bithionol to the host cell or the subject. In some embodiments of the present invention, a method of inhibiting or preventing a caspase-dependent pathogen selected from ricin, anthrax lethal toxin, Botulinum neurotoxin A, diphtheria toxin, *Pseudomonas aeruginosa* exotoxin A, cholera toxin, or Zika virus in a host cell or in a subject, includes administering about 4.2 uM to about 33.3 uM, or about 1.5 mg/kg/day to about 50.0 mg/kg/day of Bithionol to the host cell or the subject.

In some embodiments of the present invention, a method of inhibiting or preventing a caspase-dependent pathogen selected from ricin, anthrax lethal toxin, Botulinum neurotoxin A, diphtheria toxin, *Pseudomonas aeruginosa* exotoxin A, cholera toxin, or Zika virus in a host cell or in a subject, includes administering about 10 uM to about 30 uM, or about 3.0 mg/kg/day to about 50.0 mg/kg/day of Bithionol to the host cell or the subject.

In some embodiments of the present invention, a method of inhibiting or preventing a caspase-dependent pathogen selected from ricin, anthrax lethal toxin, Botulinum neurotoxin A, diphtheria toxin, *Pseudomonas aeruginosa* exotoxin A, cholera toxin, or Zika virus in a host cell or in a subject, includes administering about 6.0 mg/kg/day to about 50.0 mg/kg/day of Bithionol to the host cell or the subject.

Combination Compositions and Treatments

Some pathogens reproduce rapidly in mammals and also produce toxins that damage the host cells. Examples of such pathogens include *Bacillus anthracis, Clostridium botulinum, Vibrio cholerae* (cholera), *corynebacterium diphtheriae*, and *Pseudomonas aeruginosa*. The treatment of such pathogens may thus include preventing or inhibiting toxin damage, and for patients whose immune systems cannot destroy the bacteria, an antibiotic that destroys the bacteria. Thus, for some subjects exposed to such pathogens, treatment that combines Bithionol with an antibiotic may produce better clinical results than Bithionol alone. Non-limiting examples of antibiotics for this purpose include Octodrine (6-methylheptan-2-amine), vancomycin, clindamycin, cephaloridine, fidaxomicin, metronidazole, ciprofloxacin, doxycycline, erythromycin, penicillin, tetracycline, or combinations thereof.

In some embodiments of the present invention, a composition for treating or inhibiting a caspase-dependent pathogen, includes Bithionol and an antibiotic selected from Octodrine (6-methylheptan-2-amine), vancomycin, clindamycin, cephaloridine, fidaxomicin, metronidazole, ciprofloxacin, doxycycline, erythromycin, penicillin, tetracycline, or combinations thereof.

In some embodiments of the present invention, a composition includes Bithionol and an antibiotic in a mixture. The therapeutic amounts of antibiotics vary for each antibiotic and the therapeutic doses are known in the art and established for conventional tablets and/or parenteral (e.g., intravenous, intramuscular, subcutaneous) administration. The antibiotic dosage may vary depending on the weight of the subject and the severity of the infection. In some embodiments, the mixture of Bithionol and an antibiotic is a mixture for parenteral administration.

In some embodiments of the present invention, a composition includes Bithionol and an antibiotic selected from Octodrine (6-methylheptan-2-amine), vancomycin, clindamycin, cephaloridine, fidaxomicin, metronidazole, ciprofloxacin, doxycycline, erythromycin, penicillin, tetracycline, or combinations thereof in a mixture prepared for parenteral administration.

In some embodiments of the present invention, a composition includes a dose of about 1.5 mg/kg/day to about 50.0 mg/kg/day of Bithionol in combination with Octodrine (6-methylheptan-2-amine), vancomycin, clindamycin, cephaloridine, fidaxomicin, metronidazole, ciprofloxacin, doxycycline, erythromycin, penicillin, tetracycline or combinations thereof. In some embodiments, a composition includes a parenteral dose (e.g., IV dose) of about 1.5 mg/kg/day to about 50.0 mg/kg/day of Bithionol and a parenteral dose (e.g., IV dose) of about 1.5 mg/kg/day to about 50 mg/kg/day Octodrine (6-methylheptan-2-amine). In some embodiments, the IV dose of Octodrine is about 4 to about 50 mg/kg/day.

Octodrine is disclosed as an antibiotic against gram-negative and gram-positive bacteria in U.S. Pat. No. 9,439,876, Martchenko et al., Method of Treating Microbial Infections, the entire content of which is incorporated herein by reference.

In some embodiments of the present invention, a method of treating, inhibiting, or preventing anthrax (*Bacillus anthracis*), botulinum (*Clostridium botulinum*), *Vibrio cholerae* (cholera), diphtheria (*Corynebacterium diphtheriae*), *Pseudomonas aeruginosa* or combinations thereof includes administering Bithionol in combination with an antibiotic selected from Octodrine (6-methylheptan-2-amine), vancomycin, clindamycin, cephaloridine, fidaxomicin, metronidazole, ciprofloxacin, doxycycline, erythromycin, penicillin, tetracycline, or combinations thereof.

Administration of the Bithionol Composition

As used herein, the term "parenteral administration" and "administered parenterally" means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. The phrases "systemic administration," "administered systemically," "peripheral administration" and "administered peripherally" as used herein mean the administration of a compound, drug or other material other than directly at a site of infection, such that it enters a system of the subject (e.g., the circulatory system, the respiratory system, or through the skin) and, thus, is subject to metabolism and other like processes.

As used herein, the terms "administering" and "introducing" are used interchangeably and refer to the placement of the pharmaceutical composition including an Bithionol composition according to some embodiments of the present invention, into a living organism or cells thereof by a method or route which results in at least partial localization of the Bithionol at a desired site.

In the preparation of pharmaceutical doses of the Bithionol composition for oral administration, the composition may be mixed with solid, powdered ingredients, such as lactose, saccharose, sorbitol, mannitol, starch, arnylopectin, cellulose derivatives, gelatin, and/or another suitable ingredient, as well as with disintegrating agents and lubricating agents such as magnesium stearate, calcium stearate, sodium stearyl fumarate and/or polyethylene glycol waxes. The mixture may then be processed into granules or pressed into tablets.

The following Examples are presented for illustrative purposes only, and do not limit the scope or content of the present application.

EXAMPLES

Example 1. Identification of Host Hub Proteins Exploited by Multiple Pathogenic Toxins Cytotoxic bacterial and plant toxins have evolved to exploit host proteins and cellular pathways that mediate the entry of those toxins into host cells and to induce cell-death.

Figure 1A:
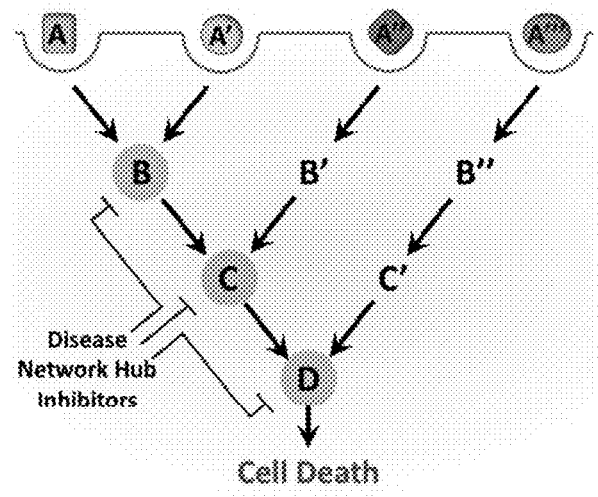
FIG. 1A is a depiction of the concept where multiple pathogenic pathways overlap, and hub proteins (purple circles) mediate multiple disease pathways, according to embodiments of the present invention.
Figure 1B:
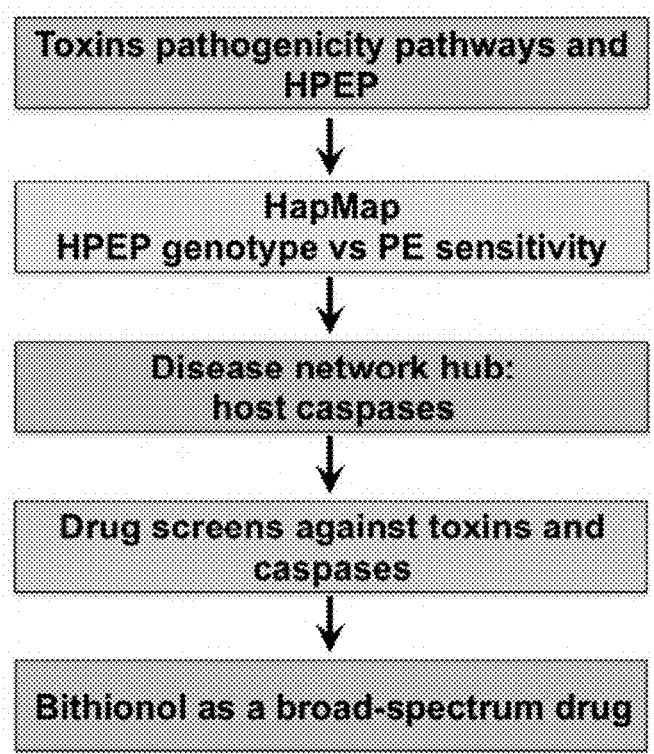
FIG. 1B is a depiction of the design of the current study in which the known host pathways and host proteins exploited by pathogens (HPEP) are considered, HapMap cell lines are used to study the association between cellular sensitivity to *Pseudomonas aeruginosa* exotoxin A (PE) and genetic mutations in genes coding for proteins exploited by PE; the mutations in host caspases associate with altered sensitivity to PE, and these proteins are defined as disease network hubs, which are used as targets for subsequent drug screens; this approach yielded the broad-spectrum host-oriented drug, Bithionol.
Figure 2A:
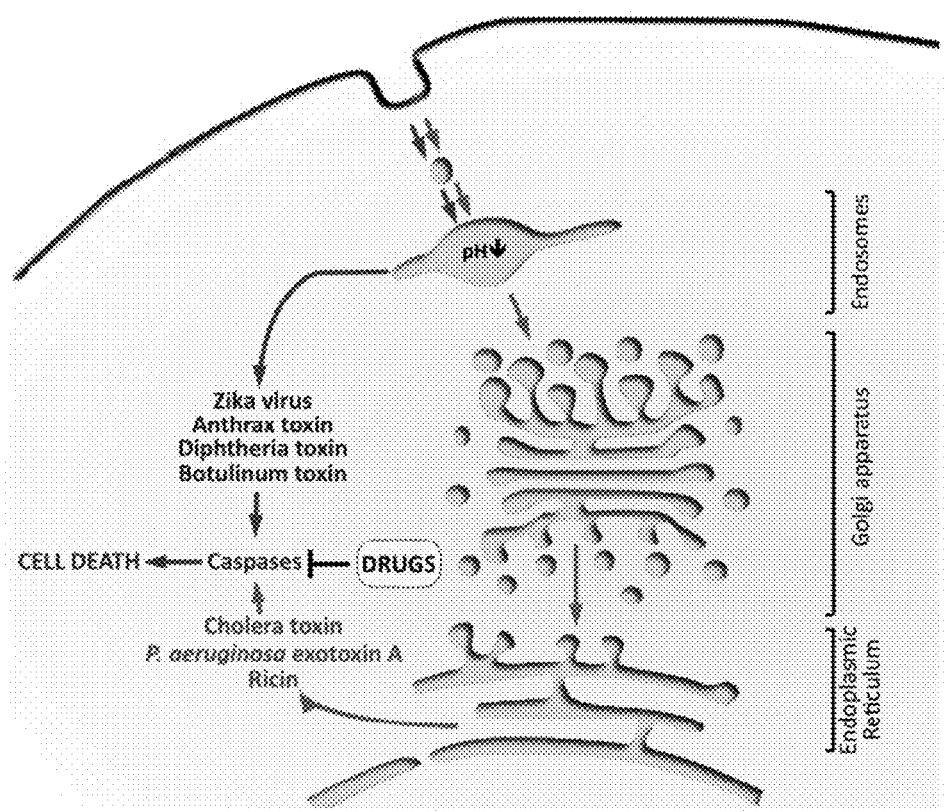
FIG. 2A is a depiction of toxins as well as their pathways that induce caspase-mediated cell death; these toxins enter into the host cytoplasm either from acidified endosomes or endoplasmic reticulum; broad-spectrum anti-toxin drugs are screened to identify inhibitors of host caspases.
Figure 2B:
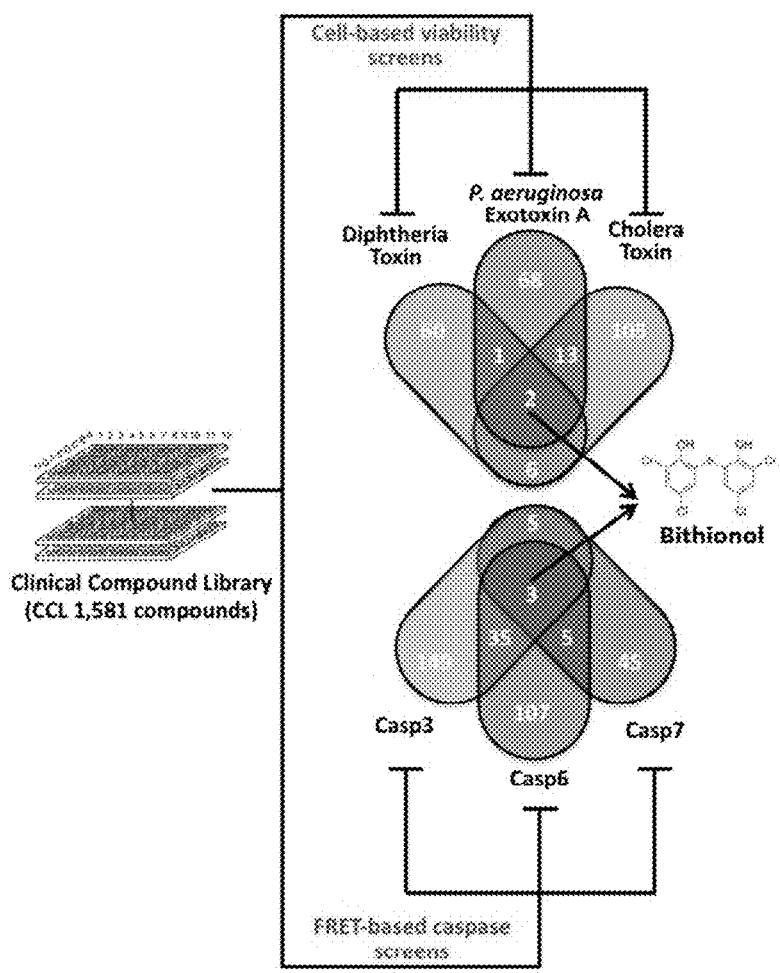
FIG. 2B is a schematic depicting the use of Clinical Compound Library (CCL) to screen for inhibitors of hubs of human disease networks in which the CCL is screened by a multiplex approach that incorporates biochemical fluorescence resonance energy transfer (FRET) and cell survival assays looking for drugs capable of simultaneously inhibiting host caspases-3/6/7 and reducing cytotoxicities of three bacterial toxins, resulting in the discovery of broad-spectrum and host-oriented drug, Bithionol, according to embodiments of the present invention.
Figure 2C:
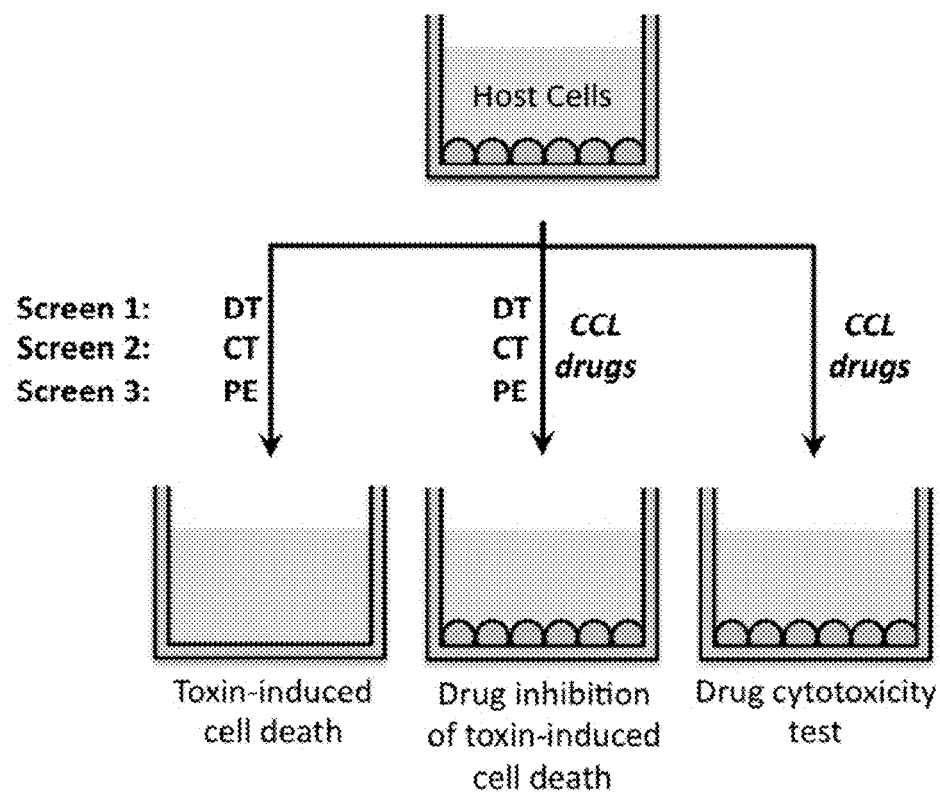
FIG. 2C is a schematic diagram of cellular screens to identify drugs that reduce cellular lethality induced by diphtheria toxin, *Pseudomonas aeruginosa* exotoxin A, and cholera toxin, according to embodiments of the present invention.
Figure 2D:
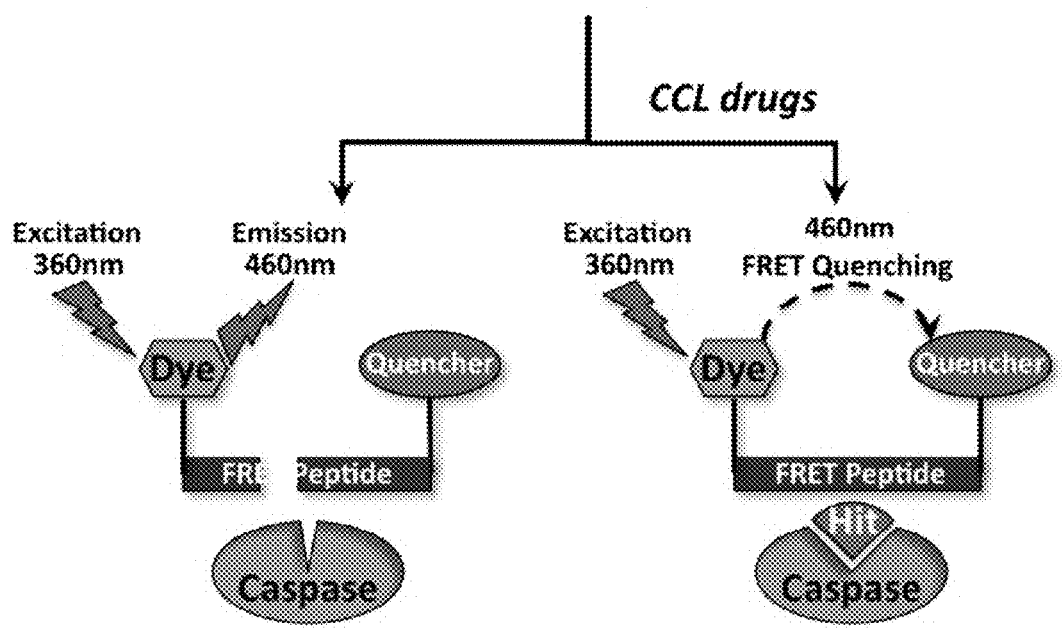
FIG. 2D is schematic diagram of a parallel FRET screen to identify drugs that inhibit proteolytic reaction of caspases-3, -6, and -7, according to embodiments of the present invention.

Although toxins exploit unique host pathways, these pathways are interconnected. While anthrax, diphtheria, and Botulinum toxins reach the cytoplasm from acidified endosomes, cholera, *Pseudomonas aeruginosa* and ricin toxins are transported into the cytoplasm through the host ER-associated degradation pathway. These pathways interconnect at host "hub" proteins. Using one of those toxins, *Pseudomonas aeruginosa* exotoxin A (PE), such hub proteins were identified by i) determining whether known genetic mutations in host proteins exploited by PE affect the sensitivity of host cells to this toxin, and ii) investigating whether these host proteins are also exploited by additional pathogenic agents. The protein hubs will be used as targets in drug screens, in order to discover broad-spectrum host-oriented anti-pathogenic agents drugs (FIG. 1B).

Example 2. The Effect of Caspase Mutations on the Sensitivity of Human B-Cells to *P. aeruginosa* Exotoxin A It has previously been shown that PE exploits several host proteins for its binding to and entry into host cells 5 and initiates programmed cell death by inducing activities of host caspase-3, -6, and -7. It was investigated whether known mutations in host proteins exploited by PE associate with altered cytotoxicity of the toxin in cells from tissues that are naturally attacked by this toxin. The availability of human B-cells, which are physiological targets of PE through the HapMap Project (Sabeti et al., 2005, Nature, 437:1299-1320, doi:10.1038/nature04226, the entire contents of which is incorporated herein by reference) provided an opportunity to test whether mutations in host proteins that constitute PE pathogenicity pathway affect the cellular sensitivity to this toxin. The initial tests with cells from a few individuals revealed that their sensitivity to PE varies greatly. Remarkably, further investigation of PE sensitivity of B-lymphoblastoid cells derived from 234 individuals in geographically and ethnically diverse human populations [87 Yoruba in Ibadan, Nigeria (YRI), 60 Utah residents with ancestry from northern and western Europe (CEU), 43 Japanese in Tokyo, Japan (JPT), and 44 Han Chinese in Beijing, China (CHB)] showed a prominent 200-fold difference in lethality to the toxin (FIGS. 3A and 3B). The range in PE sensitivity, as measured by the dose required to kill 20% of the cells [log(1/LD20)], was similar in all four human cell populations (FIG. 3C). Analysis of toxin sensitivity in parent/children trios indicated that relative sensitivity to PE is a heritable trait (P-value<0.0001) (FIG. 3D).

The widespread and unimodal distribution observed for log(1/LD20) (FIG. 3B) is likely a result of a polygenic inheritance model, consistent with evidence that multiple host proteins mediate PE lethality. To learn whether genetic variations in the genes encoding for these proteins account for any of the variation in sensitivity of B-cells to PE seen in FIG. 3A, the association of numerous previously reported mutations with PE sensitivity was tested. Caspase-7 and -3 mutations that were previously reported to associate with cancer and rheumatoid arthritis demonstrated a significant association with PE sensitivity in the individual HapMap populations (CASP7, rs3814231, CEU, P=0.01; CASP7, rs2227309, CEU, P=0.02; CASP3, rs4647601, rs4647693, and rs1049216, East Asian populations CHB and JPT combined, P=0.04 for each SNP) (FIGS. 3E-3I). These results show that the activity of caspases affects host cell sensitivity to toxins, and that these proteins are potential therapeutic intervention points and targets for the following drug screens. In addition to PE, ricin and toxins of anthrax, diphtheria, Botulinum, and cholera induce programmed cellular death by activating host caspases (FIG. 2A). Therefore, a drug screen against hub caspases is of great interest, as these proteins are exploited by multiple pathogenic pathways, and therefore caspase inhibitors can act as broad-spectrum drugs.

Example 3. A Multiplexed Cellular Screen for CCL Drugs that Inhibit Cytotoxic Activities of Bacterial Toxins Exploiting Unique but Interconnected Host Pathways In an effort to identify existing drugs that might be repurposed as novel host-oriented broad-spectrum therapies, a Clinical Compound Library (CCL) was screened through multiplex-based drug screening (FIG. 2B). Compounds were screened based on capability of both i) reducing cytotoxicities of diphtheria toxin, cholera toxin, and PE, and ii) inhibiting proteolytic activities of host caspases-3, -6, and -7 exploited by these toxins in biochemical assays (FIGS. 2B-2D). In principle, a combination of biochemical and cellular drug screens could provide drug hits that reduce toxins' cytotoxicities by inhibiting host caspases, and thus, this approach could simultaneously provide drug candidates and their protein targets.

Members of the CCL were screened for the ability to reduce cell death of host RAW264.7 and C32 cells treated with PE, cholera toxin, or diphtheria toxin (FIG. 2C). At the indicated doses, between 30 and 50 percent of RAW264.7 cells undergo cell death within 12 hours for *Pseudomonas* and cholera toxins. For C32 cells, similar cell death was observed at 24 hours exposure to diphtheria toxin under the experimental conditions employed. A "hit" in this screen was defined as an event where cells exposed to a drug increased cell survival by at least 20 standard deviations (~1% hit rate) above the survival of control cells treated with either toxin, and is not cytotoxic to cells in the absence of toxins. Events defined as "multiplex hits" interfered with cell killing by at least two toxins. The two multiplex hits that were identified as capable of reducing the cytotoxicities of all three toxins were Bithionol and Pyrogallol (FIG. 2B).

Example 4. A Multiplex Protein Function-Based Screen for CCL Drugs that Inhibit Proteolytic Activities of Host Caspase-3, -6, and -7

In parallel experiments, the CCL as screened for drugs that could inhibit the function of hub caspases-3, -6, and -7 (FIG. 2D) that mediate cytotoxicity caused by bacterial toxins used in the multiplex cellular drug screens (FIG. 2B). Caspase activities were induced in RAW264.7 cells by PE treatment. A fluorescence resonance energy transfer (FRET) assay was used to screen and identify drugs that inhibit proteolytic activities of caspases. Optimized substrate peptides for caspase-3, -6, and -3/7 proteolytic activities were used with a fluorogenic 7-amino-4-methylcoumarin group at the N-terminus and acetyl quenching group at the C-terminus. As a FRET substrate that is uniquely cleaved by caspase-7 has not been identified, and since caspases-3 and -7 are close orthologues, caspase-7 inhibitors were searched for one that could block proteolysis of a caspase-3/7-specific substrate and not caspase-3-specific substrate. After cleavage by caspase, the fluorescence of AMC at 460 nm increases, while inhibitors of caspases prevent it. Compounds that showed greater than 80% (~1% hit rate) inhibition were defined as hits and selected for re-validation and further studies. Events defined as "multiplex hits" interfered with proteolytic activities of at least two caspases. Bithionol was one of the three multiplex hits identified as capable of prominently reducing the proteolysis of all three caspase substrates (FIGS. 2B and 4A-4C). Since Bithionol was identified by both cellular and biochemical multiplex screens (FIG. 2B), the efficacy of Bithionol and the breadth of its potential as a host-oriented anti-pathogenic agent was further investigated as disclosed in subsequent examples herein.

Figure 4G:
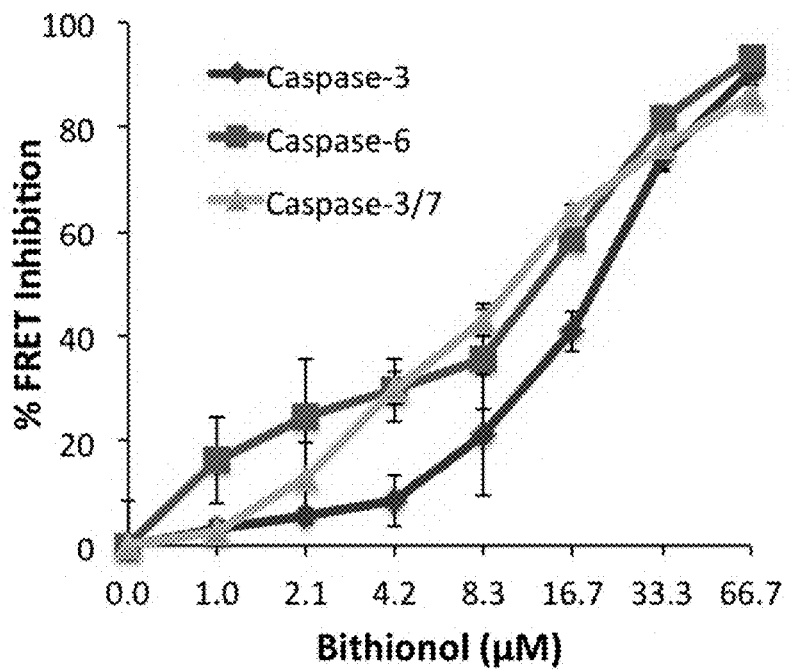
FIG. 4G is a graph of the amount of caspase inhibition measured by FRET analysis for increasing concentrations of Bithionol in cells pretreated with Pseudomonas aeruginosa exotoxin A (PE) to induce caspase activity in three independent FRET assays measuring caspase-3 (blue), caspase-6 (red), and caspase-3/7 (green), according to embodiments of the present invention.

Example 5. Bithionol Reduces the Pathogenicity of a Range of Toxins by Inhibiting Host Caspases To investigate the potency of Bithionol, drug titration curves in host RAW264.7 and C32 cells was performed. It was demonstrated that Bithionol was able to reduce diphtheria, cholera, and *Pseudomonas* toxins-mediated cytotoxicities with an EC50 of 10 μM (FIGS. 4D-4F). The effect of different concentrations of Bithionol for the ability to inhibit the proteolytic cleavage of substrates specific for cellular caspases-3, 6, and 3/7 was tested. In this test, a linear dose-dependent caspase-inhibitory efficacy of Bithionol, with IC50 of 21, 13, and 11 μM for caspases-3, -6, and -3/7, respectively were observed as shown in FIG. 4G. These results are consistent with anti-toxins EC50's of Bithionol in cellular tests (FIGS. 4D-4F).

Figure 4H:
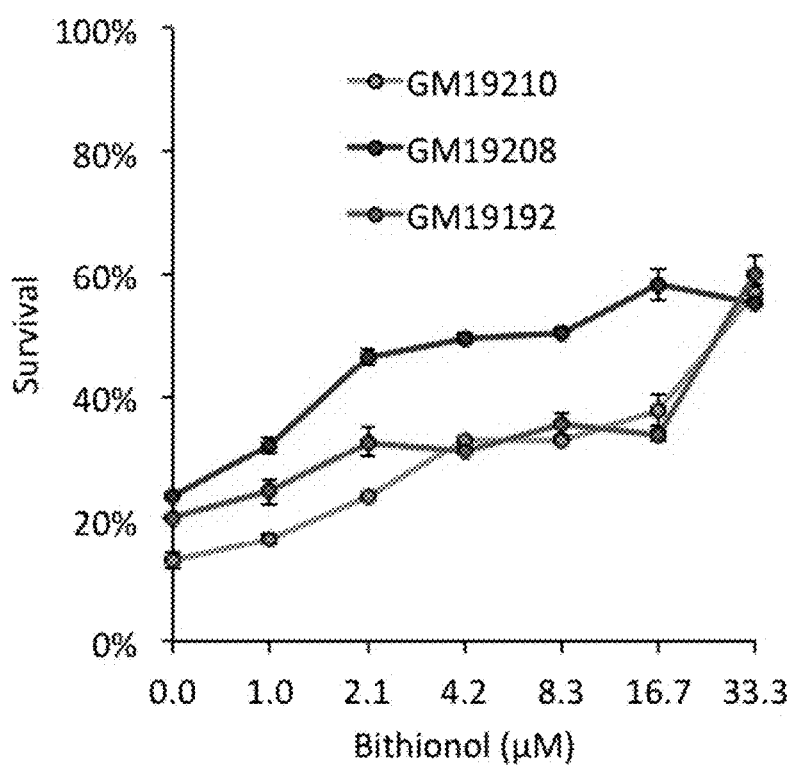
FIG. 4H is a graph of cell survival (inhibition of cytotoxicity) in human B-lymphocytes incubated with the indicated doses of Bithionol for 1 hour, and then challenged with the PE toxin for 6 hours, with cell viability determined by Alamar Blue assay and shown as the percentage of survivors relative to cells not treated with Bithionol, according to embodiments of the present invention.

Bithionol reduction of cellular sensitivity to PE in randomly selected PE-sensitive HapMap cells was also tested. From this test, it was observed that the drug protected three cell lines treated with amounts of PE sufficient to kill 80% of cells (FIG. 4H). These results confirm the anti-toxin potential of Bithionol in host cells.

Figure 4I:
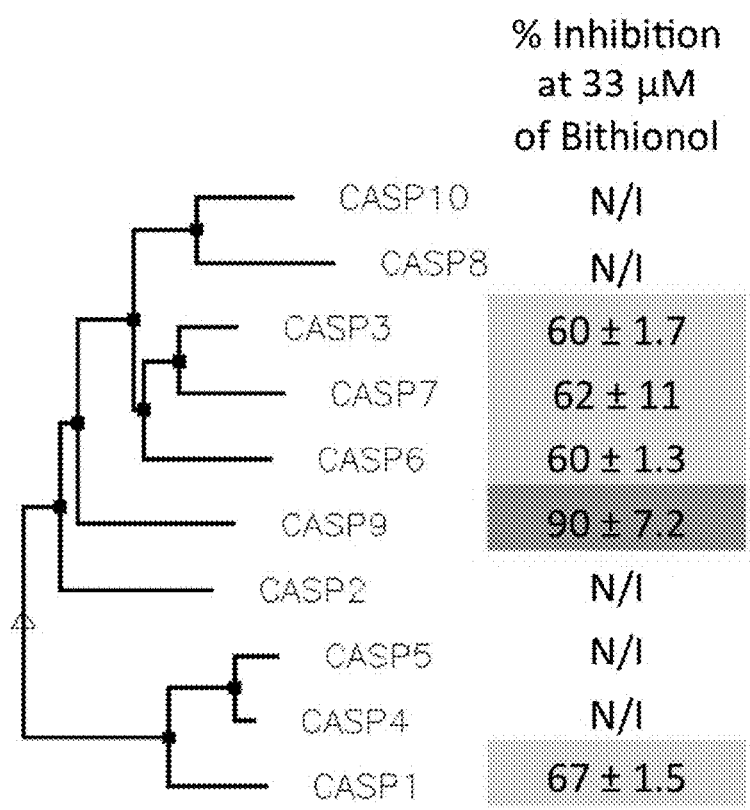
FIG. 4I summarizes the observations of Bithionol inhibition of caspases-1, -3, -6, -7, and -9 from Bithionol tested at 33 µM for its ability to inhibit FRET reactions of purified human caspases-1 through 10 with percent inhibition values shown compared to activity of caspases untreated with Bithionol with a phenogram of ten human caspases, assembled by Multalin using Dayhoff alignment parameters to demonstrate relative homology of caspases, according to embodiments of the present invention.

Humans have 10 well-characterized caspases that collectively form a pathway, often referred to as "the caspase cascade", where caspases-3, -6, and -7 are the executioners of cell death and are activated by other caspases. The ability of Bithionol to inhibit activities of ten purified recombinant human caspase proteins was tested, and it was demonstrated that in addition to caspases-3, -6, and -7, Bithionol inhibited activities of caspases-1 and -9, while having no inhibitory effects on other caspases (FIG. 4I). Together, these results demonstrate that Bithionol is a direct inhibitor of a select subset of caspases, and that it reduces cellular sensitivity to toxins by targeting at least host caspases.

Example 6. Bithionol Inhibits Cytotoxic Activity of Anthrax Toxins

Anthrax toxins, the major virulence factors of the *Bacillus anthracis* bacterium, include an exotoxin protein complex consisting of a protective antigen (PA) and lethal factor (LF) that act collectively to damage host cells. PA binds to cellular receptors, while LF acts as a protease cleaving cytoplasmic MAPKKs. Three additional host proteases mediate entry and lethality of anthrax toxin: furin, cathepsin-B, and caspase-1.

To test the ability of Bithionol to neutralize cytotoxic activity of anthrax toxin, the effect of Bithionol on cell viability in LF-PA-treated RAW264.7 cells was tested. While 80% of cells used for these assays normally undergo cell death within 6 hours of exposure to anthrax toxin, Bithionol provided substantial protection against LF-PA-mediated cell killing at 33 μM (FIG. 5A).

Caspase-1 activation, which occurs in LF-PA intoxication, was monitored using a FRET assay. While an induction of caspase-1 activity upon LF-PA treatment in the absence of Bithionol was observed, caspase-1 induction was not detected in Bithionol-treated cells challenged with anthrax toxin (FIG. 5B). This result confirms that Bithionol inhibits anthrax toxin cytotoxicity by at least inhibiting caspase-1 activity.

Figure 5C:
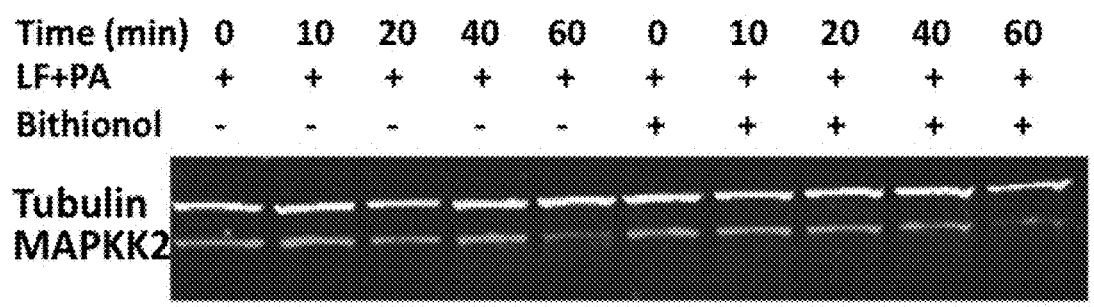
FIG. 5C is an immunoblot of MAPKK2 showing that Bithionol does not block proteolysis of cellular mitogen-activated protein kinase kinase 2 (MAPKK2) by anthrax LF toxin because MAPKK2 was cleaved in LF-PA treated RAW264.7 cells, but treatment with Bithionol did not affect this process: RAW264.7 cells were incubated with Bithionol or DMSO for 1 hour before addition of vehicle control or 1 µg/ml PA+LF for up to 60 minutes; cells were lysed and analyzed via immunoblotting with a MAPKK2-specific antibody, with tubulin used as a loading control, according to embodiments of the present invention.

The inhibition of additional anthrax toxin pathway proteases by Bithionol in live cells was also tested. By utilizing MAPKK immunoblotting (FIG. 5C), a hybrid toxin FP59 that enters host cells by utilizing PA, but kills cells by LF-independent mechanism (FIGS. 5D, 5E), and cathepsin-B FRET assay (FIG. 5F), it was demonstrated that Bithionol does not inhibit proteolytic activities of cellular LF, furin, and cathepsin-B.

Figure 3A:
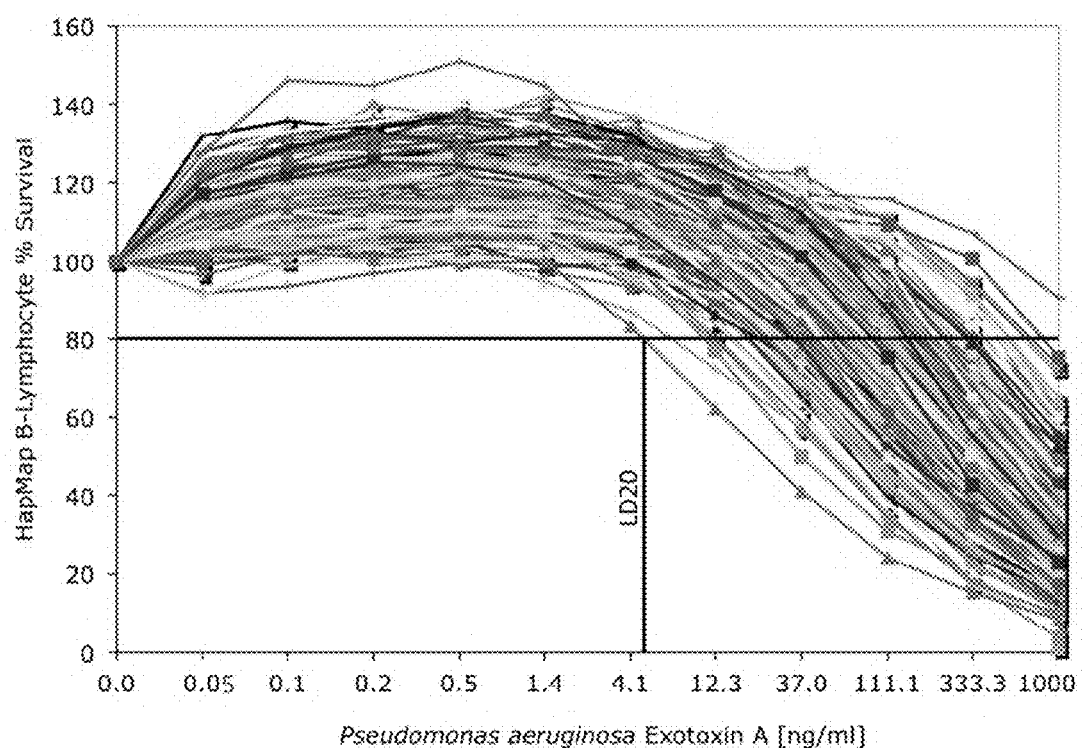
FIG. 3A shows a graph of the effect of Bithionol on *P. aeruginosa* exotoxin A (PE) in human 234 B-lymphocytes treated with PE at concentrations as shown with the percent (%) survival being relative to cells treated with PE alone, and an LD20 calculation (lethal dose for killing 20% of the total cells) for the most sensitive cell line shown as an example, according to embodiments of the present invention.
Figure 3B:
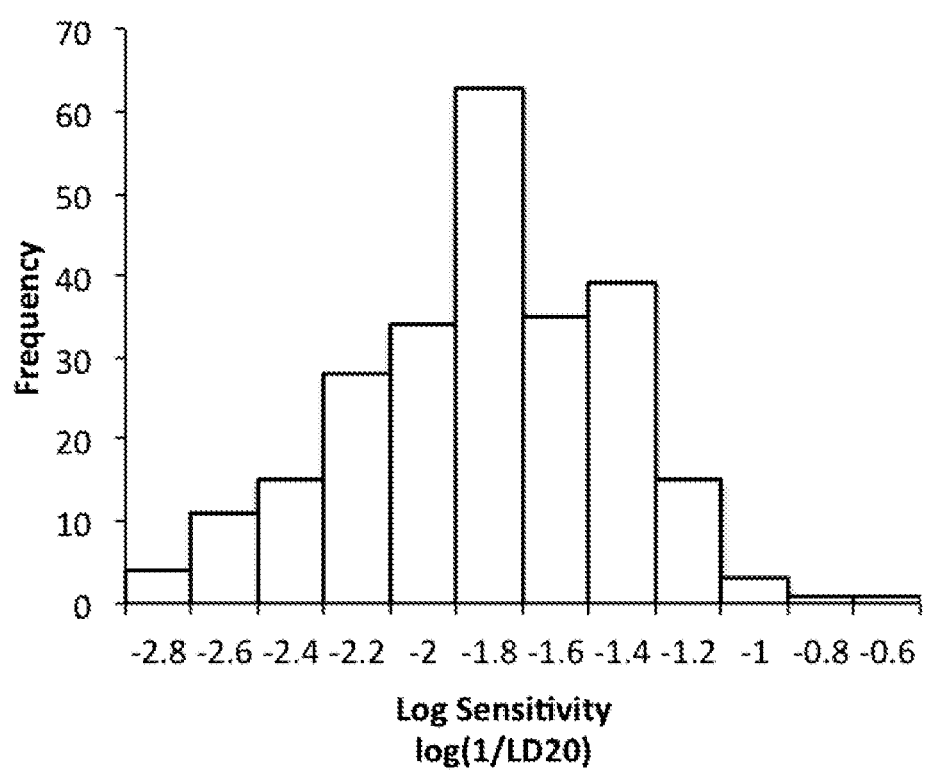
FIG. 3B is a graph of the LD20 values (ng/ml of PE) of human 234-B lymphocytes treated with PE in which the LD20 values were calculated and expressed on an inverse log 10 scale in which PE sensitivity is defined numerically as 1/LD20, according to embodiments of the present invention.
Figure 3C:
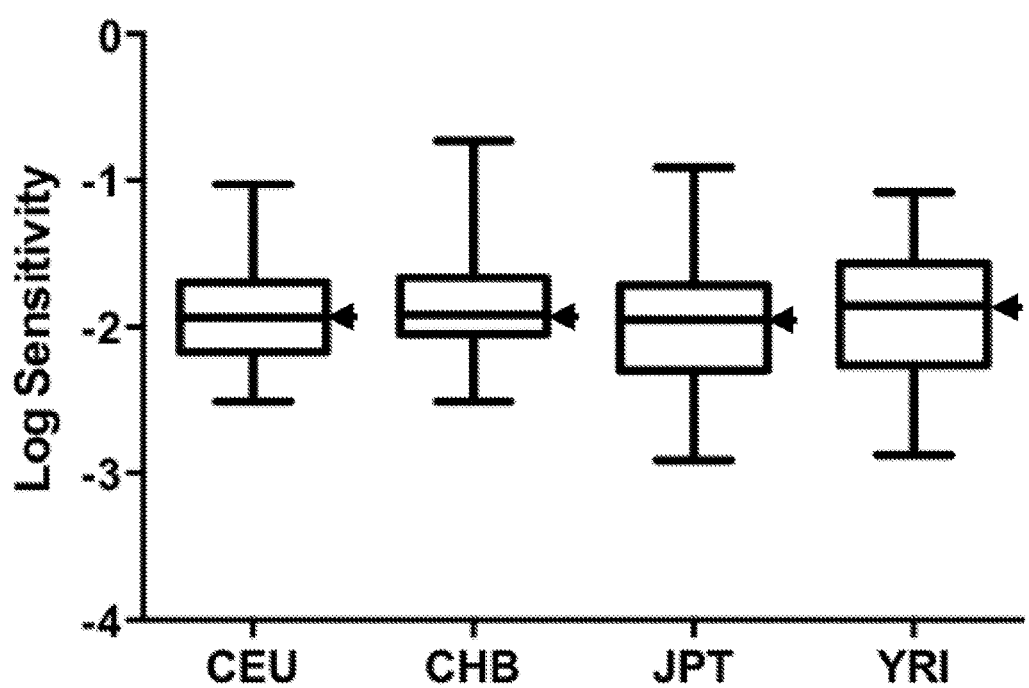
FIG. 3C is graph of population-specific distribution of PE toxin sensitivities in populations of CEU (European), CHB (Chinese Han), JPT (Japanese), or YRI (Yoruba), with the black bar representing the median log sensitivity, with the box extending from the lower to the upper quartile and the whiskers extending to the most extreme data point, according to embodiments of the present invention.
Figure 3D:
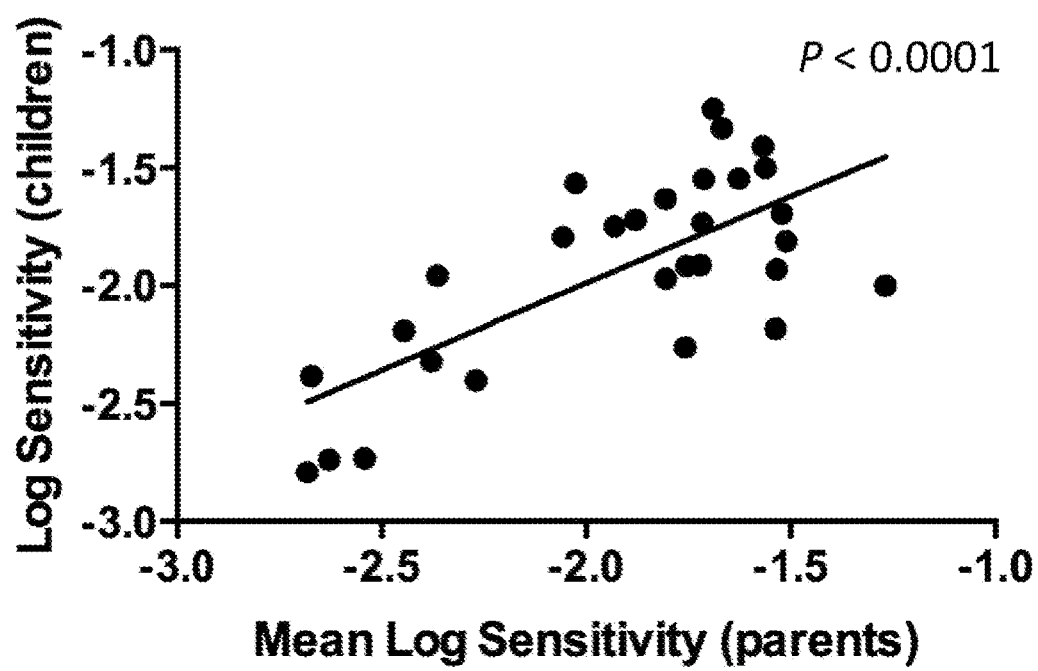
FIG. 3D is a graph of heritability of log sensitivity in Yoruba trios in which the plot is the log toxin sensitivity of the children against the mean log toxin sensitivity of the parents, and the heritability is estimated as the slope (0.74) of the regression of the children phenotype on the midparent phenotype, according to embodiments of the present invention.
Figure 3E:
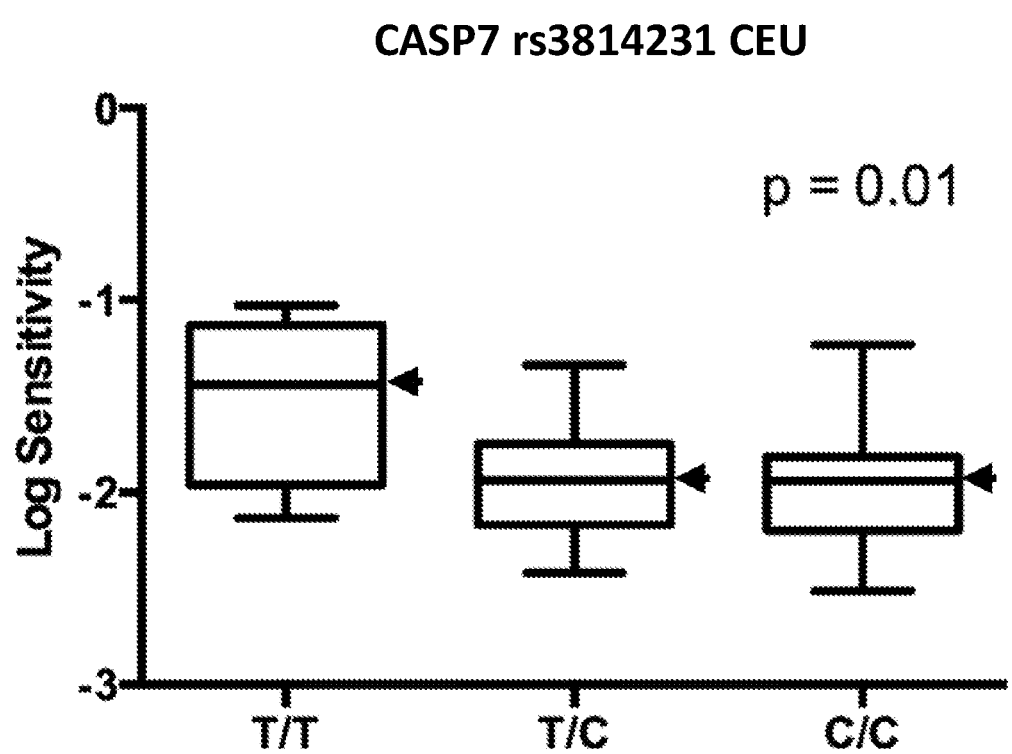
FIG. 3E is a graph showing caspase-7 single nucleotide polymorphism (SNP) rs3814231 associates with log PE sensitivity, according to embodiments of the present invention.
Figure 3F:
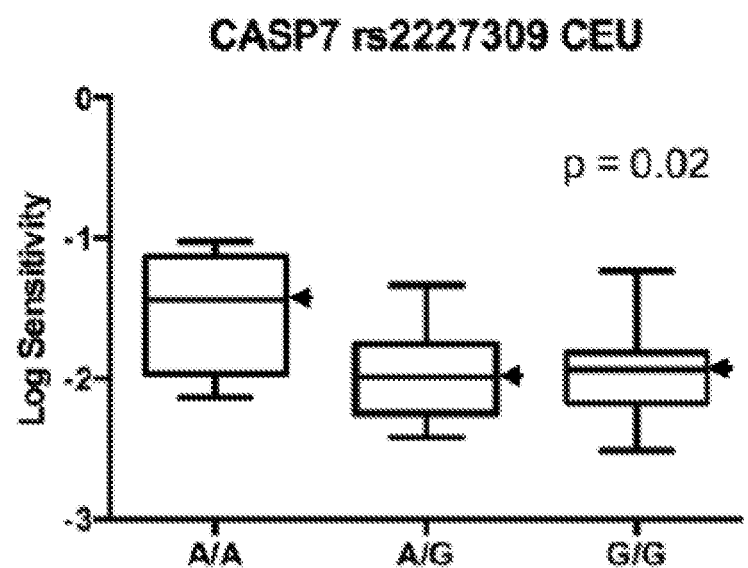
FIG. 3F is a graph showing caspase-7 SNP rs2227309 associates with log PE sensitivity in CEU populations, according to embodiments of the present invention.
Figure 3G:
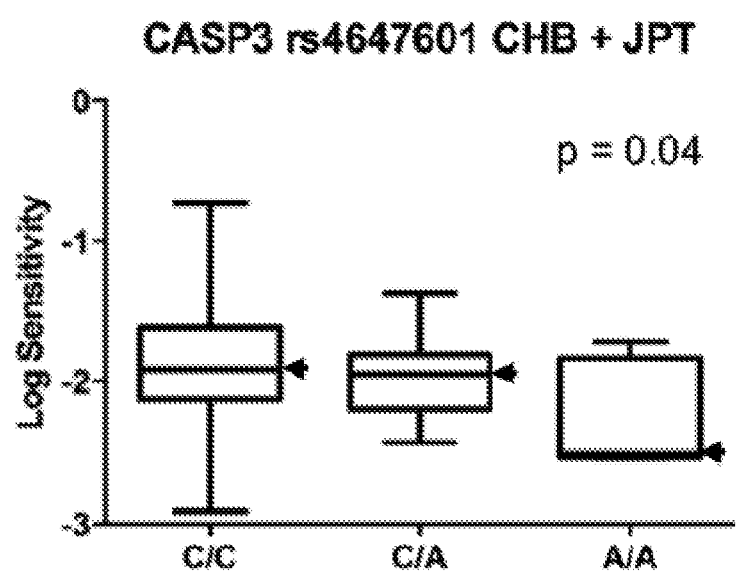
FIG. 3G is a graph showing caspase-3 SNP rs4647601 associates with log PE sensitivity in combined CHB and JPT populations, according to embodiments of the present invention.
Figure 3H:
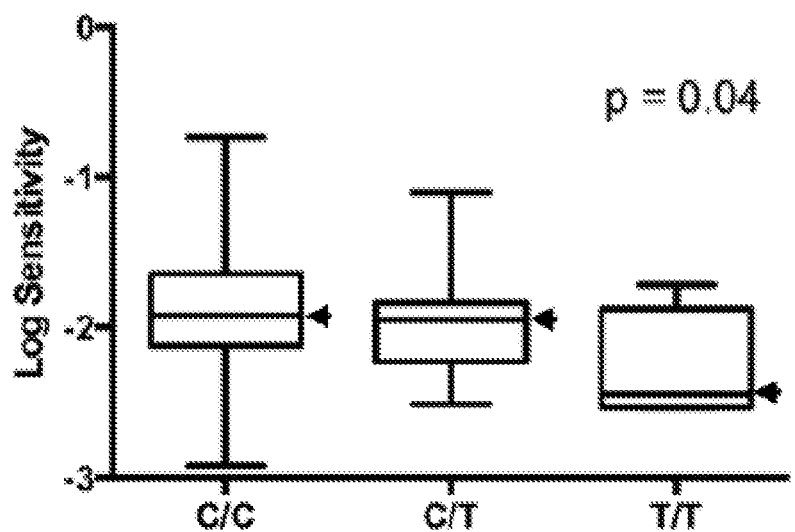
FIG. 3H is a graph showing caspase-3 SNP rs4647693 associates with log PE sensitivity in combined CHB and JPT populations, according to embodiments of the present invention.
Figure 3I:
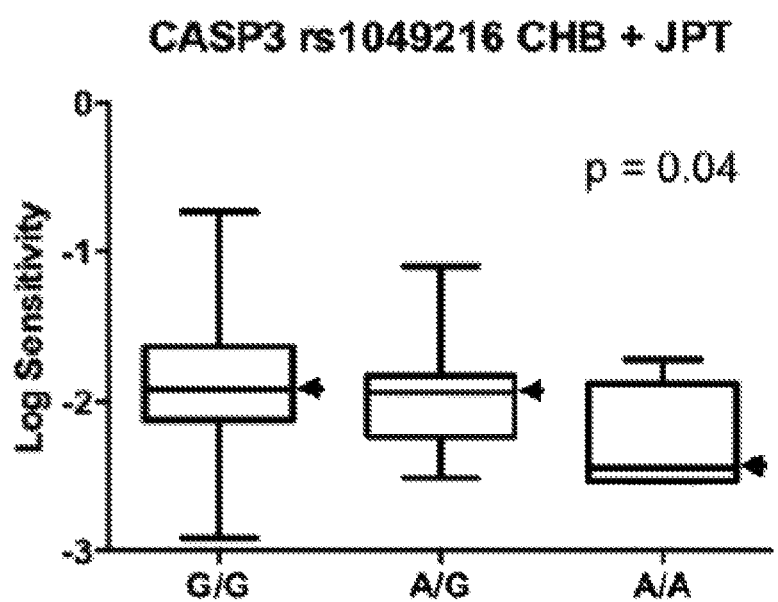
FIG. 3I is a graph showing caspase-3 SNP rs1049216 associates with log PE sensitivity in combined CHB and JPT populations, according to embodiments of the present invention.

Example 7. Bithionol Inhibits Ricin and Botulinum Neurotoxin A-Induced Death In Vitro and In Vivo Ricin is another toxin known to induce host caspases-3, -6, and -7 as described in Komatsu et al., 1998, *Journal of Biochemistry*, 124:1038-1044 and Wahome et al., 2012, *PloS one*, 7: e49075, doi:10.1371/journal.pone.0049075, the entire contents of both of which are incorporated herein by reference. It reaches the mammalian cytoplasm through the retrograde transport route from the plasma membrane to ER via endosomes and the Golgi apparatus (FIG. 3A). Once in the cytoplasm, ricin inhibits cellular protein synthesis by cleaving a glycosidic bond within the large rRNA of the 60S subunit of eukaryotic ribosomes. The ability of Bithionol to reduce ricin-mediated cellular killing was tested, and it was observed that the drug was able to reduce toxin-mediated cytotoxicity with an EC50 of 10 μM (FIG. 6A).

Botulinum neurotoxin serotype A (BoNT/A) is a protease that translocates into the host cytoplasm from acidic endosomes, where it cleaves the synaptosome-associated protein, SNAP-25, and inhibits neurotransmitter release among neurons, leading to muscular paralysis 26. BoNT/A has been reported to cause cellular caspases-3 and -7-dependent apoptosis as described in Lourenssen, et al., *American journal of physiology. Gastrointestinal and liver physiology*, 2009, 297: G228-239, doi:10.1152/ajpgi.90705.2008, the entire contents of which is incorporated herein by reference.

After oral administration, Bithionol crosses the intestinal epithelium and is absorbed into the bloodstream in humans and many animals. The efficacy of Bithionol as a therapeutic agent during BoNT/A intoxication in Swiss Webster mice was tested. Animals were given a lethal oral dose of BoNT/A complex in the presence and absence of Bithionol. Ninety percent of animals that received a lethal dose of BoNT/A without Bithionol died within 3 days of intoxication (FIG. 6B). All mice that were challenged with BoNT/A and treated with Bithionol at 6.0 mg/kg, survived without displaying toxin-associated symptoms, such as wasp waist and paralysis (FIG. 6B).

Figure 6D:
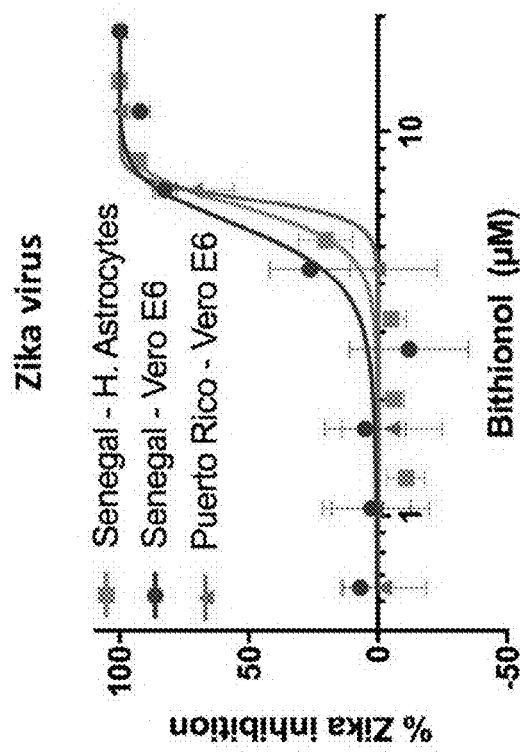
FIG. 6D is a graph of the percent amount of Zika virus (ZIKV) inhibition as a function of Bithionol concentration (uM) in host Vero E6 cells (Senegal Vero E6 cells in red and Puerto Rico Vero E6 cells in green) and Senegal astrocytes (orange) as measured by fluorescent microscopy, according to embodiments of the present invention.
Figure 6C:
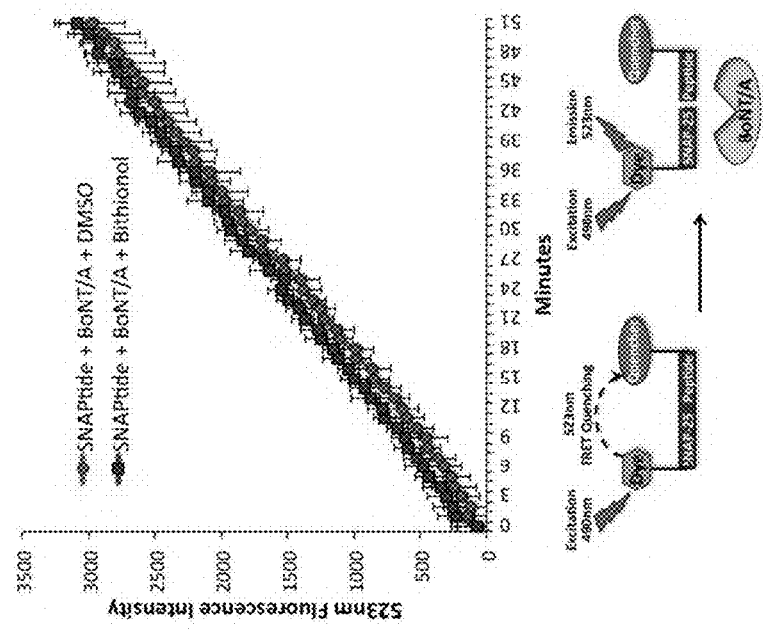
FIG. 6C is a graph showing the amount of fluorescence intensity from two FRET cell lysate reactions in which 5 nm BoNT/A light chain cleaves fluorescently labeled SNAP-25 substrate peptide without Bithionol (DMSO) (red) or in the presence of 33 µM Bithionol (blue), according to embodiments of the present invention.

Since BoNT/A acts as a protease, it was investigated whether Bithionol directly inhibits the proteolytic activity of BoNT/A by utilizing a FRET assay. An optimized SNAP-25 peptide with a fluorogenic FITC group at the N-terminus and DABCYL quenching group at the C-terminus was used as the substrate. After cleavage by BoNT/A the fluorescence of FITC at 523 nm increases. It was determined that Bithionol did not affect the proteolysis rate of the fluorescent substrate (FIG. 6C). This result shows that Bithionol protects mice by inhibiting host targets, rather than by inhibiting the toxin itself.

Example 8. Bithionol Acts as a Zika Virus Inhibitor

In addition to pathogenic toxins, viruses are also known to propagate by activating host caspases and inducing programmed cell death as described in Mocarski et al., 2012, *Nature reviews. Immunology,* 12:79-88, doi:10.1038/nri3131, the entire content of which is incorporated herein by reference. Similar to toxins, Zika virus (ZIKV) has been reported to lead to cell-death by inducing host caspase-3 and neuronal apoptosis during its propagation as described in Tang et al., *Cell stem cell,* 2016, doi: 10.1016/j.stem.2016.02.016 and Dang et al., 2016, *Cell stem cell,* doi: 10.1016/j.stem.2016.04.014, the entire contents of both of which are incorporated herein by reference. Moreover, caspases have previously been reported to cleave various viral proteins, affect viral protein localization, promote viral genome replication and viral assembly, and have been reported to be necessary for viral replication and propagation as described in Wurzer et al., 2003, *The EMBO journal,* 22:2717-2728, doi:10.1093/emboj/cdg279 and Richard and Tulasne, 2012, *Cell death & disease,* 3, e277, doi:10.1038/cddis.2012.18, the entire contents of both of which are incorporated herein by reference.

Upon observing that Bithionol protects cells from caspase-inducing toxins, it was hypothesized that Bithionol might also be able to inhibit the pathogenicity of the Zika virus. The strains utilized in this study were chosen to gauge the ability of Bithionol to inhibit Zika virus strains found within both ZIKV lineages. Both strains utilized in this study had low passage histories and had intact glycosylation sites. Furthermore, both strains were geographically and genetically divergent. Puerto Rico Zika strain, PRVABC59, is closely related to virus strains circulating in the New World including those strains isolated in Brazil and Guatemala. The African ZIKV lineage is ancestral to the Asian lineage; as such DAK AR D 41525 was selected as it is a low passage strain that is mycoplasma free. The ability of Bithionol to inhibit Senegal and Puerto Rico isolates of ZIKV in infected Vero E6 cells and human astrocytes was tested. In order to detect infected cells, immuno-staining was performed using anti-Flavi-virus envelope protein antibodies. Bithionol inhibited the abundance of Puerto Rico ZIKV in Vero E6 cells with a half maximal effective concentration (EC50) of 6.7 µM as well as Senegal ZIKV in Vero E6 and human astrocytes with EC50's of 5.5 and 6.3 µM respectively (FIG. 6D, 6E). These data indicate that Bithionol is effective in inhibiting ZIKV in host cells.

Example 9. Material and Methods

Chemicals and reagents. All bacterial toxins were purchased from List Biological Laboratories (Campbell, Calif.). FP59 was a gift from Stephen Leppla (NIAID). Ricin was purchased from Vector Laboratories. Clinical Compound Library (CCL) drug library was purchased from Johns Hopkins University Bloomberg School of Public Health. Bithionol was repurchased from Sigma-Aldrich.

Cell culture and cell lines. RAW264.7 mouse macrophage and human C32 melanoma cells (ATCC CRL-1585) were maintained in DMEM (Sigma-Aldrich). Human B-lymphocytes were grown in IMDM (Invitrogen). Human K562 chronic myelogenous leukemia cells (ATCC CCL-243) were grown in RPMI 1640 Medium (Invitrogen). Vero E6 (ATCC CRL-1586) were maintained in MEM (Corning). Primary human Astrocytes (NHA-Astrocytes-AGM, Lonza, #CC-2565) were cultured in Astrocyte Basal Medium (Clonetics ABM, Lonza) supplemented with AGM SingleQuot Kit Supplement and Growth factors (CC-4123). All media were supplemented with FBS, penicillin, and streptomycin.

Human B-lymphocytes sensitivity to *Pseudomonas* toxin-mediated lethality: Human B lymphocytes were treated with serial dilutions of *P. aeruginosa* exotoxin A for 48 hours. The viability of B cells was determined by Alamar Blue (AbD Serotec, BioRad) fluorescence, as described by the manufacturer. Each data point shown in FIG. 3A represents the average and standard deviation (SD) of results from three wells. Cell viability is shown as the percentage of survivors obtained relative to cells in the absence of the toxin (100% survival). LD20 was calculated for each cell line. Statistical analysis and graphical presentation were performed using GraphPad Prism software. A P value<0.05 was considered statistically significant. Homozygous medians were compared by an unpaired t test. CHB and JPT, two East Asian populations, were pooled in order to obtain a more accurate estimate of effect size in the larger combined population. Because linear regression is sensitive to outliers, one outlier in CHB was removed, as the log sensitivity of this cell line could not be determined within the toxin range tested.

Cellular drug screens. RAW264.7 cells (10,000 per well) were seeded in 96-well plates 24 hours before the assay. Cells were treated with compounds for 1 hour, and then challenged with either 2 µg/ml PE or 4 µg/ml cholera toxin for 12 hours. As rodent cells are insensitive to diphtheria toxin, C32 cells were treated with 2 µg/ml of diphtheria toxins for 24 hours. Determination of RAW264.7 and C32 viability was performed by MTT (3-(4,5-dimethylthiazol-2-yl)-2,5-diphenyltetrazolium bromide) assay. Cell viability is defined as the percentage of surviving cells obtained relative to cells treated with DMSO (100% survival).

Caspases FRET drug tests. Caspases were induced in RAW264.7 by treating cells with 2 µg/ml of PE for 4 hours. Caspases were extracted and their activity was measured using Caspase Assay Kit (Sigma-Aldrich) with or without drugs.

The FRET reaction was performed in 96 well plates, and each reaction contained 16 µM substrate peptides (Peptides International) conjugated with a 7-amino-4-methylcoumarin group at the N-terminus and acetyl group at the C-terminus. The amino acid sequences of substrates were: DNLD for caspase-3, DQTD for caspases-3 and -7, and VEID for caspase-6. CCL compounds were tested at the final concentration of 33 µM, as pilot testing indicated that CCL screen at 16 µM would not yield a sufficient number of multiplex hits. Reactions were initiated by adding caspase-containing lysate to a final concentration of 6 µg/ml. Kinetic measurements were obtained at 37° C. every 5 minutes for 2 hours using a fluorescent plate reader. Excitation and emission wavelengths were 360 nm and 460 nm, respectively, with a cutoff wavelength of 365 nm. Rates of reactions were quantified by the Microsoft Excel LINEST function. A BioVision kit was used to test Bithionol's ability to inhibit FRET reactions of purified recombinant human caspases-1 through 10. One unit of caspase was used in a single FRET reaction.

Toxins treatments and cell viability assays. Cells (10,000 per well) were seeded in 96-well plates 24 hours before the assay. Cells were treated with Bithionol for 1 hour. RAW264.7 cells were challenged with anthrax toxins that include LF or FP59 and PA83 or PA63 (for 6 hours), PE (for 12 hours), or cholera toxin (for 12 hours) at 0.5, 2, and 4 µg/ml respectively. C32 cells were treated with 2 µg/ml of diphtheria toxin for 24 hours. Determination of cells viability was performed by MTT assay. B-lymphocytes cells were seeded in a 96-well plates at 10,000 cells/well 1 hour before toxin treatment, treated with Bithionol for 1 hour, and then challenged with 8 µg/ml PE for 6 hours. Determination of lymphocyte viability was determined by Alamar Blue (AbD Serotec, BioRad) fluorescence, as described by the manufacturer. Each data point shown for MTT and Alamar Blue assays indicates the mean±SD (standard deviation) value obtained in triplicate assays done in a representative experiment. At least three such experiments were carried out.

MAPKK2 cleavage assay. N-terminal MAPKK2, anti-tubulin, and anti-PA antibodies were purchased from Santa Cruz Biotechnology. RAW264.7 cells were pre-treated with 33 µM of Bithionol for 1 hour. Following pre-treatment, the cells were exposed to 0.5 µg/ml of PA and LF at 37° C. for up to three hours in the presence of 33 µM of Bithionol. The cells were then washed with cold PBS five times and lysed with RIPA buffer containing a protease inhibitor mixture (Santa Cruz Biotechnology, Inc.). Cell lysates were quantified using the BCA protein quantification kit (Pierce) and loaded onto 4-12% denaturing gels (Criterion XT Precast Gel, Bio-Rad). After electrophoresis for several hours, the gel was transferred overnight to nitrocellulose membranes; membranes were probed with anti-MAPKK2 or anti tubulin antibodies. Quantitative Western blot analyses of the bands were accomplished using the Odyssey infrared imaging system (LI-COR Biosciences).

Cellular cathepsin B and caspase-1 activity assays. Cathepsin B and caspase-1 activities in total cell lysates were determined using an InnoZyme cathepsin B activity assay kit (EMD Milipore) and caspase activity assay kit (BioVision), performed according to the manufacturers' instructions. Cellular cathepsin B or caspase-1 activities with and without Bithionol were tested by pre-treating cells with 33 µM of Bithionol for 1 hour, followed by lysing cells and testing protease activities with fluorescently labeled specific substrates. Caspase-1 activities were induced by 1 hour pretreatment of cells with 0.5 µg/ml of LF+PA, and was compared to cells un-induced by the toxin. Fluorescence intensities indicating cathepsin B or caspase-1 activities were measured (Molecular Devices, Spectra Max 384 PLUS).

Ricin treatment and cell viability assay. K562 cells were seeded at a density of 2×105 cells/well in 24-well plates. Cells were pre-treated with Bithionol for 2 hours and 0.4 ng/ml ricin was added to the treated wells. Following the 24-hour ricin treatment, the percent of viable cells (within the live gate by FSC/SSC) was measured by flow cytometry using a BD Accuri C6 Flow Cytometer. The experiment was performed in duplicate for each condition.

Mice intoxication studies. 10 Swiss Webster (CFW) mice (6 week old) were treated with 0.125 mg/mouse Bithionol in the presence or absence of BoNT/A complex (3 µg/mouse, Metabiologics, Madison Wis.) in phosphate gelatin buffer (0.028 M sodium phosphate pH 7.0, 0.2% gelatin) by oral gavage. Animals were observed over a period of 7 days. Methods were carried out in accordance with approved guidelines. All experiments were performed in accordance with relevant guidelines and regulations. All animal experiments have been approved by the Western Regional Research Center IACUC. Euthanasia protocols follow recommendations established by the American Medical Veterinary Association Guideline for Euthanasia to minimize animal pain and suffering.

BoNT/A light chain FRET assay. The reaction volume was 250 μl per well in 96 wells plate, containing 50 mM HEPES pH 7.4 containing 0.05% TWEEN 20, 5 μM SNAPtide (BoNT/A substrate peptide) conjugated with DABCYL and FITC (List Biological Laboratories, Inc), and 33 μM of Bithionol. Reactions were initiated by adding BoNT/A light chain to a final concentration of 5 nM. Kinetic measurements were obtained at 37° C. every 1 min for 50 min using a fluorescent plate reader. Excitation and emission wavelengths were 490 nm and 523 nm, respectively, with a cutoff wavelength of 495 nm. At least three such FRET experiments were carried out.

Zika virus high content imaging infections assay. Strains from both ZIKV lineages (African and Asian) were used to assess the potential for Bithionol to inhibit viral abundance. ZIKV strain DAK AR D 41525 was originally isolated from a pool of *Aedes africanus* mosquitoes in Senegal in 1984 (passage history: AP61#1, C6/36#1, Vero 3) and strain PRVABC59 was originally isolated from human sera in Puerto Rico in 2015 (passage history: Vero 6). Cells were pre-treated with Bithionol for 2 hours prior to infection. Vero E6 cells were exposed to ZIKV at an MOI of 0.5; astrocytes were infected with ZIKV at an MOI of 15. Infection was terminated after 48 hours by fixing samples in formalin solution. For visualization of Zika infection cells were treated for 1 hour with anti-Flavi-virus envelop protein monoclonal antibody 4G2, followed by anti-mouse IgG conjugated with Dylight488 (Thermo). Cells were stained with Hoechst (Life Technologies) for nuclei staining and with Cell Mask Red (Life technologies) for cytoplasm staining. Nuclei were stained with Draq5 (Biostatus) diluted in PBS buffer. Images were acquired on the Opera imaging plate reader (Perkin Elmer) and analyzed using Harmony and Acapella PE software. A detailed protocol is described in the supplemental file.

As disclosed throughout, for example in FIGS. 4A, 4B, 4C, 4D, 4E, 4F, 5A, 5B, 6A, 6B, and 6D, Bithionol inhibits caspase-dependent pathogens, thereby providing a method for treating subjects infected with these pathogens.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A method of inhibiting a pathogenic agent in a host cell or in a subject, the method comprising administering Bithionol to the host cell or the subject, the pathogenic agent being selected from the group consisting of ricin, anthrax toxin, Botulinum neurotoxin A, diphtheria toxin, *Pseudomonas aeruginosa* exotoxin A, cholera toxin, Zika virus, and combinations thereof.

2. The method of claim 1, wherein the Bithionol is administered at a dose of about 1.5 mg/kg/day to about 50.0 mg/kg/day based on the weight of the subject.

3. The method of claim 1, further comprising administering an antibiotic.

4. The method of claim 3, wherein the antibiotic is selected from the group consisting of octodrine, vancomycin, clindamycin, cephaloridine, fidaxomicin, metronidazole, ciprofloxacin, doxycycline, erythromycin, penicillin, and tetracycline.

5. The method of claim 1, wherein the pathogenic agent is Botulinum neurotoxin A.

6. The method of claim 1, wherein the pathogenic agent is ricin.

7. The method of claim 1, wherein the pathogenic agent is Zika virus.

8. The method of claim 5, wherein the Bithionol is administered at a dose of about 1.5 mg/kg/day to about 50.0 mg/kg/day and the antibiotic comprises penicillin, the penicillin being administered at a dose of about 1.5 mg/kg/day to about 50 mg/kg/day based on the weight of the subject.

9. A composition for inhibiting a pathogenic agent in a host cell or a subject, the pathogenic agent being selected from the group consisting of Botulinum neurotoxin A, *Bacillus anthracis*, *Pseudomonas aeruginosa*, cholera, diphtheria, *Clostridium botulinum* and combinations thereof, the composition comprising:
  Bithionol; and
  an antibiotic.

10. The composition of claim 9, wherein the pathogenic agent is selected from Botulinum neurotoxin A.

11. The composition of claim 9, wherein the antibiotic is selected from the group consisting of octodrine, vancomycin, clindamycin, cephaloridine, fidaxomicin, metronidazole, ciprofloxacin, doxycycline, erythromycin, penicillin, tetracycline, and combinations thereof.

12. The composition of claim 9, wherein the antibiotic comprises penicillin.

13. The composition of claim 9, wherein the antibiotic comprises penicillin, the Bithionol is at a dose of about 1.5 mg/kg/day to about 50.0 mg/kg/day, and the penicillin is at a dose of about 1.5 mg/kg/day to about 50 mg/kg/day based on the weight of the subject.

14. A method of inhibiting a caspase-dependent pathogenic agent in a host cell or in a subject, the method comprising administering Bithionol to the host cell or the subject, wherein the caspase-dependent pathogenic agent is selected from the group consisting of ricin, anthrax toxin, Botulinum neurotoxin A, diphtheria toxin, *Pseudomonas aeruginosa* exotoxin A, cholera toxin, Zika virus, and combinations thereof.

15. The method of claim 14, wherein the Bithionol is administered at a dose of about 1.5 mg/kg/day to about 50.0 mg/kg/day based on the weight of the subject.

16. The method of claim 14, further comprising administering an antibiotic.

17. The method of claim 16, wherein the antibiotic is selected from the group consisting of octodrine, vancomycin, clindamycin, cephaloridine, fidaxomicin, metronidazole, ciprofloxacin, doxycycline, erythromycin, penicillin, tetracycline, and combinations thereof.

18. A composition for inhibiting a caspase-dependent pathogenic agent in a host cell or a subject, the composition comprising:
  Bithionol; and
  an antibiotic.

19. The composition of claim 18, wherein the antibiotic is selected from the group consisting of octodrine, vancomycin, clindamycin, cephaloridine, fidaxomicin, metronidazole, ciprofloxacin, doxycycline, erythromycin, penicillin, tetracycline, and combinations thereof.

* * * * *